US012633416B2

(12) United States Patent
Sinclair et al.

(10) Patent No.: US 12,633,416 B2
(45) Date of Patent: May 19, 2026

(54) METHODS FOR GEOLOCATION-BASED SKIN SCIENCE-DRIVEN ENVIRONMENTAL EXPOSURE METRICS

(71) Applicant: L'Oreal, Paris (FR)

(72) Inventors: Nicholas Sinclair, San Diego, CA (US); Fred Orsita, Wayne, NJ (US)

(73) Assignee: L'Oreal, Paris (FR)

( * ) Notice: Subject to any disclaimer, the term of this patent is extended or adjusted under 35 U.S.C. 154(b) by 257 days.

(21) Appl. No.: 18/358,772

(22) Filed: Jul. 25, 2023

(65) Prior Publication Data

US 2025/0037871 A1     Jan. 30, 2025

(51) Int. Cl.
*G16H 50/30* (2018.01)
*G16H 10/20* (2018.01)
*G16H 40/67* (2018.01)

(52) U.S. Cl.
CPC ............. *G16H 50/30* (2018.01); *G16H 10/20* (2018.01); *G16H 40/67* (2018.01)

(58) Field of Classification Search
CPC ......... G16H 50/30; G16H 10/20; G16H 40/67
USPC ....................................................... 705/2–3
See application file for complete search history.

(56) References Cited

U.S. PATENT DOCUMENTS

| | | | | |
|---|---|---|---|---|
| 11,405,184 B2 * | 8/2022 | Kosecoff | ................. | G06F 21/64 |
| 11,693,471 B2 | 7/2023 | Kosecoff | | |
| 11,790,750 B2 | 10/2023 | Kosecoff | | |
| 11,798,057 B2 | 10/2023 | Kosecoff | | |
| 12,027,268 B2 * | 7/2024 | Kosecoff | ................ | G16H 10/60 |
| 2015/0102208 A1 * | 4/2015 | Appelboom | .......... | G01J 1/4204 |
| | | | | 250/208.2 |
| 2021/0236863 A1 | 8/2021 | Suwanto et al. | | |
| 2023/0039222 A1 | 2/2023 | Jagannathan et al. | | |

FOREIGN PATENT DOCUMENTS

| | | |
|---|---|---|
| FR | 3119034 A1 | 7/2022 |
| WO | 2022093567 A1 | 5/2022 |

OTHER PUBLICATIONS

Bocheva et al., (Jun. 22, 2023), Environmental Air Pollutants Affecting Skin Functions with Systemic Implications, International Journal of Molecular Sciences, 24(13), 10502, https://doi.org/10.3390/ijms241310502 (Year: 2023).*
Preliminary Search Report and Written Opinion for FR Pat. App. 2310115, dated Apr. 8, 2024. 6 pages.

* cited by examiner

*Primary Examiner* — Joy Chng
(74) *Attorney, Agent, or Firm* — Christensen O'Connor Johnson Kindness PLLC

(57) ABSTRACT

Methods for communicating risk of skin conditions due to exposure to sunlight and environmental conditions to individuals. Methods utilize geolocation data and environmental data to provide guidance and enable consumers to make informed decisions regarding outdoor activities, healthcare, and skincare. A photopollution metric is a function of ultraviolet index (UVI) and the level of a pollutant such as particulate matter (PM) and enables communication of risk of exposome-induced skin conditions to an individual based on environmental exposure.

10 Claims, 21 Drawing Sheets

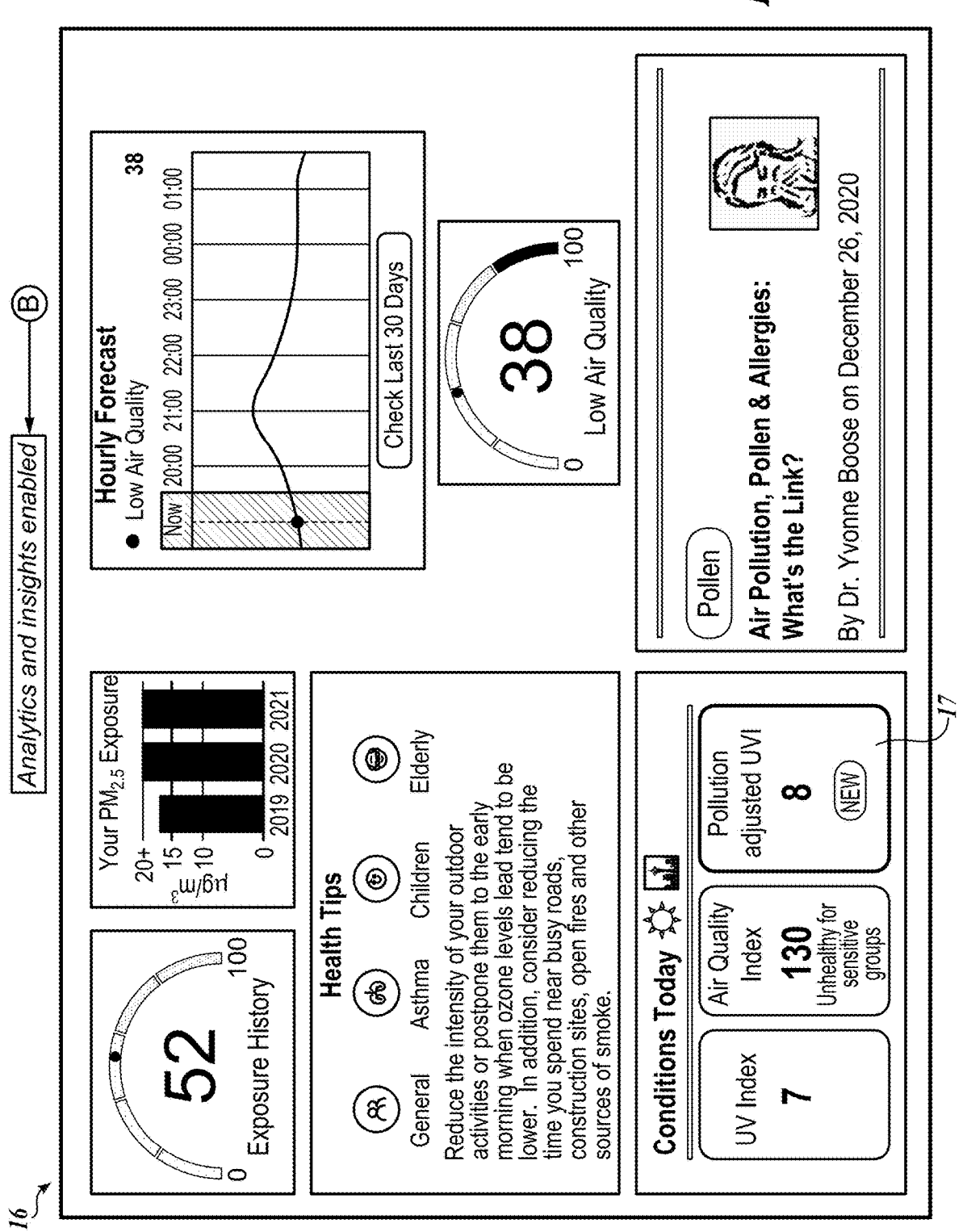

*Analytics and insights enabled*

Ⓑ

Hourly Forecast
● Low Air Quality
Now  20:00  21:00  22:00  23:00  00:00  01:00    38
Check Last 30 Days 38
Low Air Quality
0    100

Air Pollution, Pollen & Allergies: What's the Link?
By Dr. Yvonne Boose on December 26, 2020
Pollen Your PM$_{2.5}$ Exposure
20+
15
10
0
µg/m³
2019  2020  2021

Health Tips
General  Asthma  Children  Elderly

Reduce the intensity of your outdoor activities or postpone them to the early morning when ozone levels tend to be lower. In addition, consider reducing the time you spend near busy roads, construction sites, open fires and other sources of smoke.

52
Exposure History
0    100

Conditions Today ☼

UV Index
7

Air Quality Index
130
Unhealthy for sensitive groups

Pollution adjusted UVI
8
NEW

Platform Data Scope
Algo and Simple Logics Specified

*21*

| Category | Environmental Variable | Temeral Resolution | Personal History Coverage | Non-Personal Forecast Coverage | Simple Logic 1 (Mean) | Simple Logic 2 (Mean) | Simple Logic 3 (Max.) | Simple Logic 4 (Not specified) | Simple Logic 5 (Not specified) | Algo Logic 1 (Photo-pollution) | Algo Logic 2 (Dryness Index) |
|---|---|---|---|---|---|---|---|---|---|---|---|
| Solar Radiation | UV Index (UVI) | Hourly | 1 year | 5 days (daily max.) | x | | | | | | |
| | UVA/UVB | N/A | N/A | N/A | | | | | | | |
| | HEV | N/A | N/A | N/A | | | | | | | |
| Air Pollution | PM₂.₅ | Hourly | 1 year | 96 hours | x | | | | | | |
| | PM₁₀ | Hourly | 1 year | 96 hours | x | | | | | | |
| | O₃ | Hourly | 1 year | 96 hours | x | | | | | | |
| | NO₂ | Hourly | 1 year | 96 hours | x | | | | | | |
| | SO2 | Hourly | 1 year | 96 hours | | x | | | | | |
| | CO | Hourly | 1 year | 96 hours | | x | | | | | |
| | Photo-pollution (PM₂.₅ x UV) | Hourly | 1 year | N/A | | | | | | x | |
| | PAH | No | N/A | N/A | | | | | | | |
| Weather | Temperature | Hourly | 1 year | 120 hours | | x | | | | | |
| | Relative Humididity | Hourly | 1 year | 120 hours | | x | | | | | |
| | Pollen | Daily | 1 year | 2 days (daily) | | x | x | | | | |
| | Dryness Index (Temp. x RH) | Hourly | 1 year | N/A | | | | | | | x |
| | | | | | Allocated: 5/5 | Allocated: 5/5 | Allocated: 1/5 | Allocated: /5 | Allocated: /5 | Allocated: 1/5 | Allocated: 1/5 |

*FIG. 2*

Research Methods

Overview

*43*

$$\vec{S}_{kv\text{-}eff} = \vec{S}_{sr} * \vec{S}_{ft} * \vec{S}_{kv}$$

S_SR = 1  # W/M^2

Research Methods
Path to the Photo-Pollution Metric

 Finally, translating cell viability model coefficients to a photo-pollution/UVI model A. UV intensity $\longrightarrow$ UV index B. PM concentration $\longrightarrow$ Ambient PM$_{2.5}$ concentration $\longrightarrow$ Estimating PM concentration in the skin from ambient PM concentration The biological dose of PM in the skin can be modeled as follows:

$$PM_{bio\text{-}dose} = PM_{ambient} * \gamma * \beta * \alpha * \frac{1}{\psi} * t$$

where:

- $PM_{ambient}$ is the ambient air concentration of PM$_{2.5}$ in $\frac{ug}{m^3}$,
- $\gamma$ is the unitless bioaccessibility ratio, i.e., the penetration of particulate matter into the blood stream from the total amount inhaled,
- $\alpha$ is the unitless ratio of cutaneous blood output to total cardiac blood output,
- $\psi$ is the total volume of the skin organ in $\frac{1}{mL}$,
- $t$ is time in *min*.

45

| ACHIEVING | $UVI_{PP} = UVI + A * (UVI * PM_{2.5})$ |
|---|---|

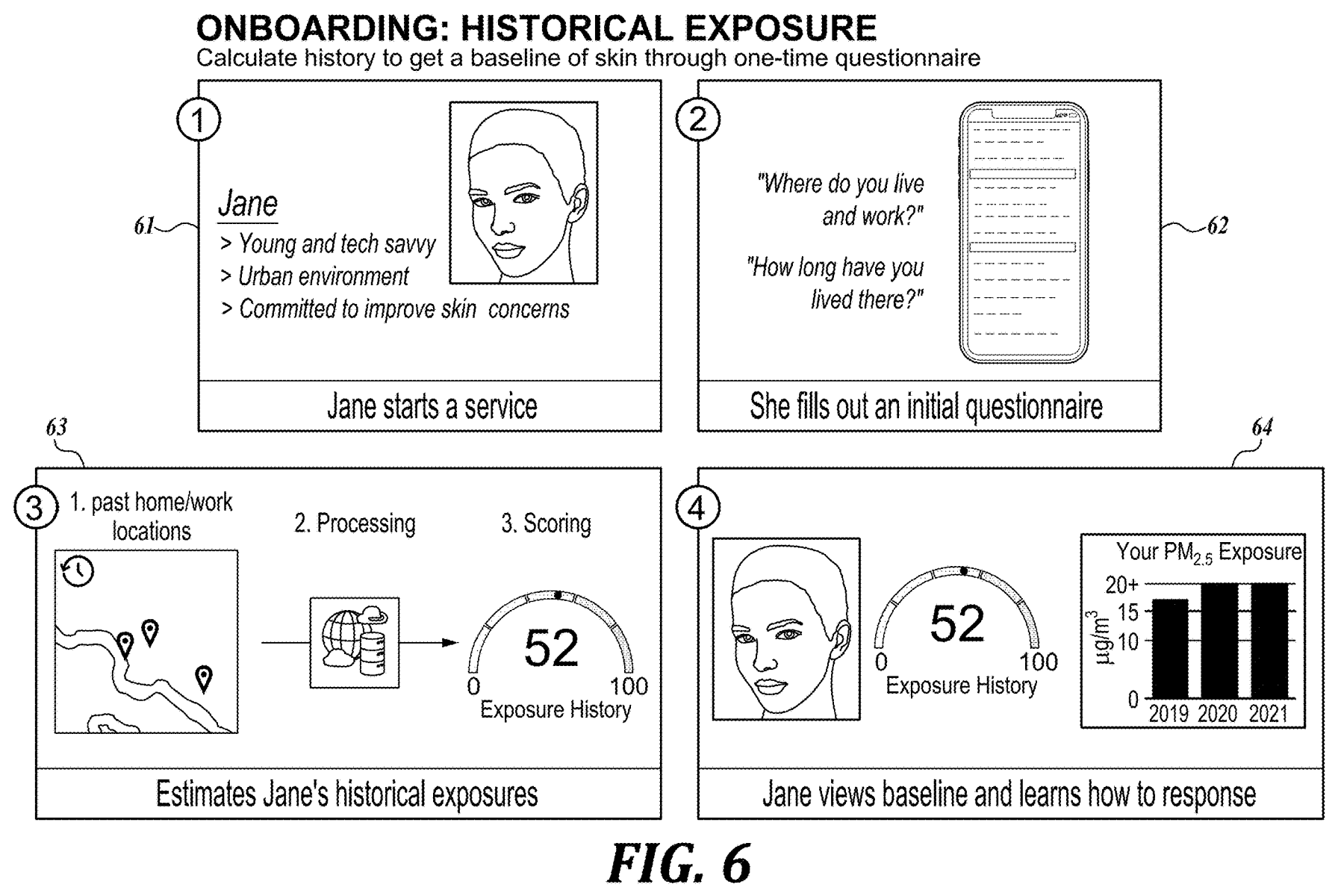

ONBOARDING: HISTORICAL EXPOSURE
Calculate history to get a baseline of skin through one-time questionnaire ① *Jane*
> Young and tech savvy
> Urban environment
> Committed to improve skin concerns Jane starts a service ② *"Where do you live and work?"*

*"How long have you lived there?"*

She fills out an initial questionnaire

③ 1. past home/work locations    2. Processing    3. Scoring

52    Exposure History    0    100

Estimates Jane's historical exposures

④ Your PM₂.₅ Exposure $\mu g/m^3$    20+  15  10  0    2019 2020 2021

52    Exposure History    0    100

Jane views baseline and learns how to response

*FIG. 6*

COACHING: DAY-TO-DAY TRACKING
Hyper-local personal exposure calculations across environmental exposures ① Jane signs up for app ② App accumulates Janes's locations ③ Algorithms estimate exposures ④ Jane receives actionable, relevant guidance

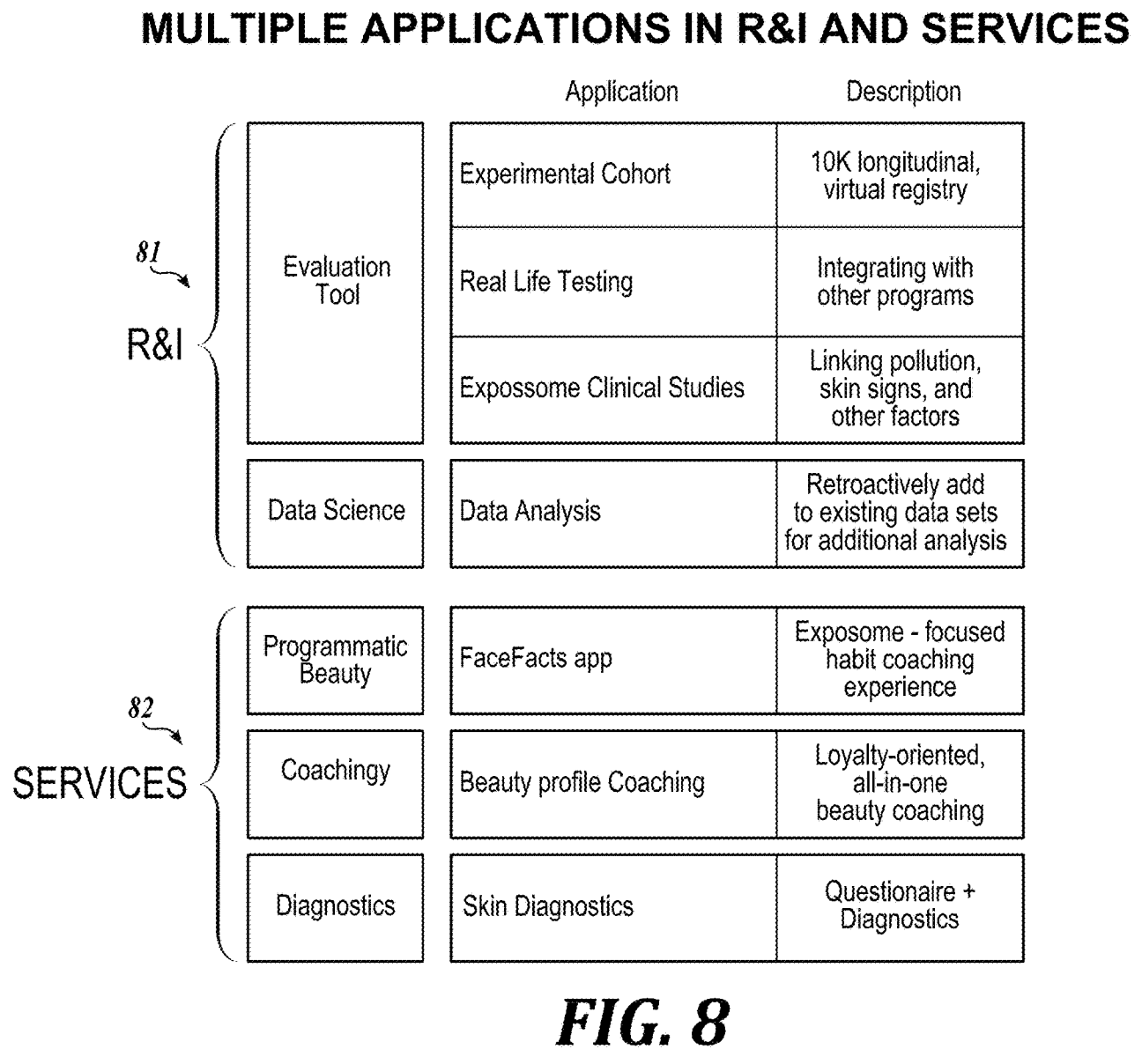

MULTIPLE APPLICATIONS IN R&I AND SERVICES

| | Application | Description |
|---|---|---|
| Evaluation Tool | Experimental Cohort | 10K longitudinal, virtual registry |
| | Real Life Testing | Integrating with other programs |
| | Expossome Clinical Studies | Linking pollution, skin signs, and other factors |
| Data Science | Data Analysis | Retroactively add to existing data sets for additional analysis |

*81* R&I

| | Application | Description |
|---|---|---|
| Programmatic Beauty | FaceFacts app | Exposome - focused habit coaching experience |
| Coachingy | Beauty profile Coaching | Loyalty-oriented, all-in-one beauty coaching |
| Diagnostics | Skin Diagnostics | Questionaire + Diagnostics |

*82* SERVICES

*FIG. 8*

All this data captured passively

| Environmental Variable | | Temeral Resolution | Personal History Coverage | Non-Personal Forecast Coverage |
|---|---|---|---|---|
| Solar Radiation | UV Index (UVI) | Hourly | 1 year | 5 days (daily max.) |
| | UVA/UVB | N/A | N/A | N/A |
| | HEV | N/A | N/A | N/A |
| Air Pollution | $PM_{2.5}$ | Hourly | 1 year | 96 hours |
| | $PM_{10}$ | Hourly | 1 year | 96 hours |
| | $O_3$ | Hourly | 1 year | 96 hours |
| | $NO_2$ | Hourly | 1 year | 96 hours |
| | SO2 | Hourly | 1 year | 96 hours |
| | CO | Hourly | 1 year | 96 hours |
| | Photo-pollution ($PM_{2.5}$ x UV) | Hourly | 1 year | N/A |
| | PAH | N/A | N/A | N/A |
| Weather | Temperature | Hourly | 1 year | 120 hours |
| | Relative Humididity | Hourly | 1 year | 120 hours |
| | Pollen | Daily | 1 year | 2 days (daily) |
| | Dryness Index (Temp. x RH) | Hourly | 1 year | N/A |

96

D

Studies enabled by smartphones, guaranteed location

*FIG. 9*
*(CONT.)*

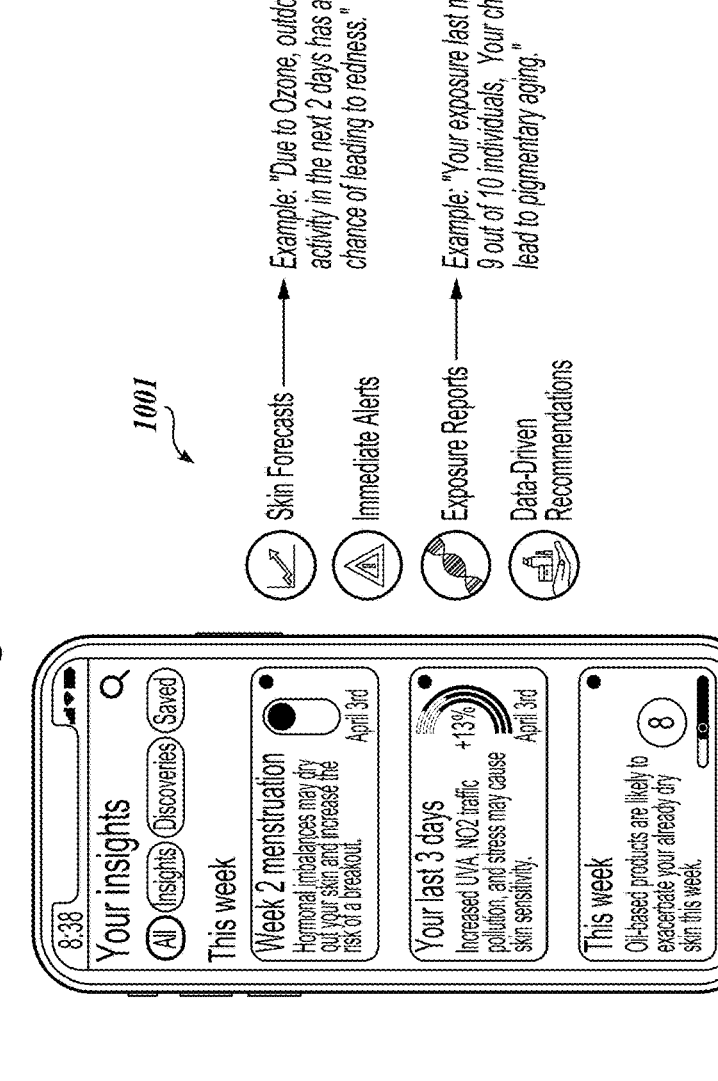

FaceFacts
Exposome-focused habit coaching

For the first time unlock

1) A complete picture of exposures

2) Powerful, personalized, and actionable insights

Skin Forecasts → *Example: "Due to Ozone, outdoors activity in the next 2 days has a medium chance of leading to redness."*

Immediate Alerts

Exposure Reports → *Example: "Your exposure last month was more severe than 9 out of 10 individuals. Your chronic exposures could mainly lead to pigmentary aging."*

Data-Driven Recommendations

*FIG. 10*

R&I Clinical App
Proposed user experience
1205
PASSIVE LOCATION SHARING
User phone movement recorded without user intervention
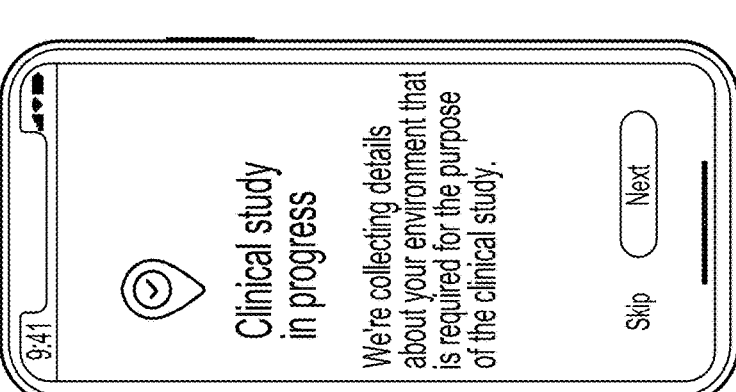
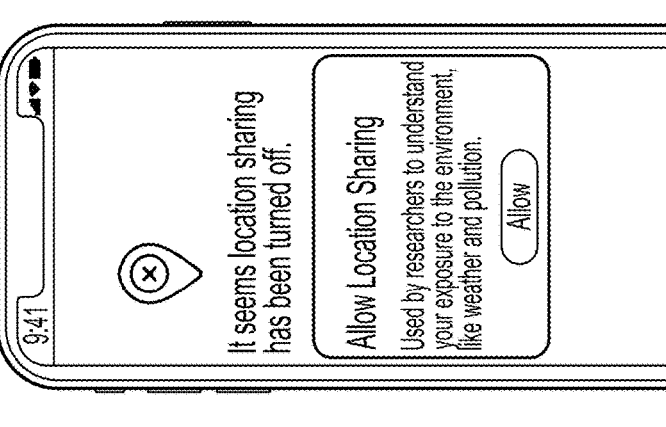
1206
END OF STUDY
App auto-terminate data collection at study conclusion
*FIG. 12*
*(CONT.)*

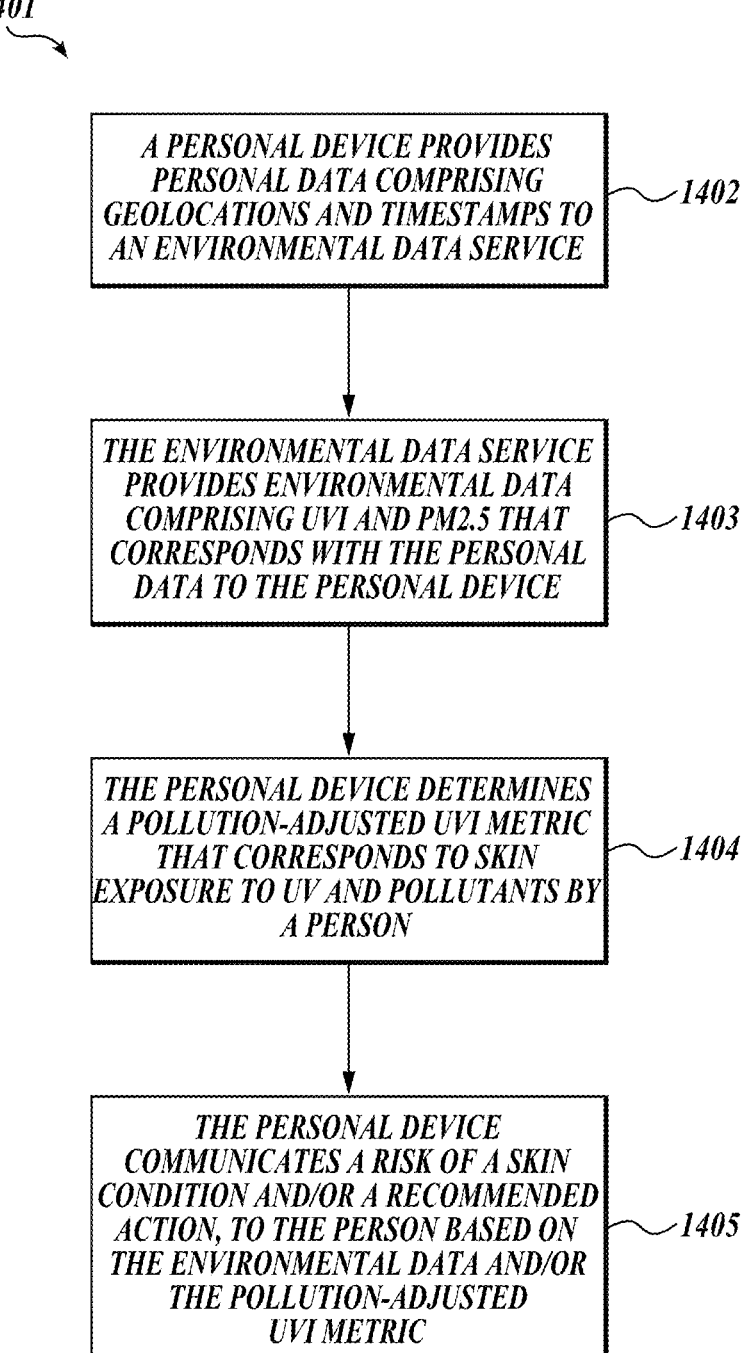

*1401*

*A PERSONAL DEVICE PROVIDES PERSONAL DATA COMPRISING GEOLOCATIONS AND TIMESTAMPS TO AN ENVIRONMENTAL DATA SERVICE* — *1402*

*THE ENVIRONMENTAL DATA SERVICE PROVIDES ENVIRONMENTAL DATA COMPRISING UVI AND PM2.5 THAT CORRESPONDS WITH THE PERSONAL DATA TO THE PERSONAL DEVICE* — *1403*

*THE PERSONAL DEVICE DETERMINES A POLLUTION-ADJUSTED UVI METRIC THAT CORRESPONDS TO SKIN EXPOSURE TO UV AND POLLUTANTS BY A PERSON* — *1404*

*THE PERSONAL DEVICE COMMUNICATES A RISK OF A SKIN CONDITION AND/OR A RECOMMENDED ACTION, TO THE PERSON BASED ON THE ENVIRONMENTAL DATA AND/OR THE POLLUTION-ADJUSTED UVI METRIC* — *1405*

*FIG. 14*

METHODS FOR GEOLOCATION-BASED SKIN SCIENCE-DRIVEN ENVIRONMENTAL EXPOSURE METRICS

SUMMARY

In an aspect, the disclosure provides a method for managing environmental exposure and associated risk of an exposome-induced skin condition of a subject, the method comprising: determining an ultraviolet index (UVI) and a geolocation-specific pollutant level responsive to one or more inputs indicative of a geolocation of the subject at a time: determining a value of a photo-pollution metric ($UVI_{photopollution}$) responsive to one or more inputs indicative of the UVI and the geolocation-specific pollutant level, wherein the value of the photo-pollution metric corresponds to an associated exposure risk of the exposome-induced skin condition; and communicating the associated exposure risk of the exposome-induced skin condition to the subject.

In an aspect, the disclosure provides a method for managing environmental exposure and associated risk of an exposome-induced skin condition of a subject, the method comprising: determining a geolocation-specific exposome level: determining the associated risk of the exposome-induced skin condition based on the geolocation-specific exposome level; and communicating the associated risk of the exposome-induced skin condition to the subject.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

FIG. 2 shows example environmental data that can be utilized for a metric of a device, system, or method according to the disclosure.

FIG. 6 shows a graphic visualization of an example onboarding process that utilizes a questionnaire to estimate a subject's historical exposures and baseline exposure level.

FIG. 8 shows a table outlining example uses of the metric for consumer applications.

FIG. 10 shows an example application of the metric for exposure to one or more environmental pollutants (e.g., "exposome") with a graphical user interface and/or a feedback interface for assisting consumers with decision-making in areas related to their environment, lifestyle, biological processes, and forecasting for potential exposures in the future.

FIG. 14 shows an example of a method for determining a value of a metric and communicating associated risk of an exposome-induced skin condition, according to the disclosure, using a computational system.

Figure 1:
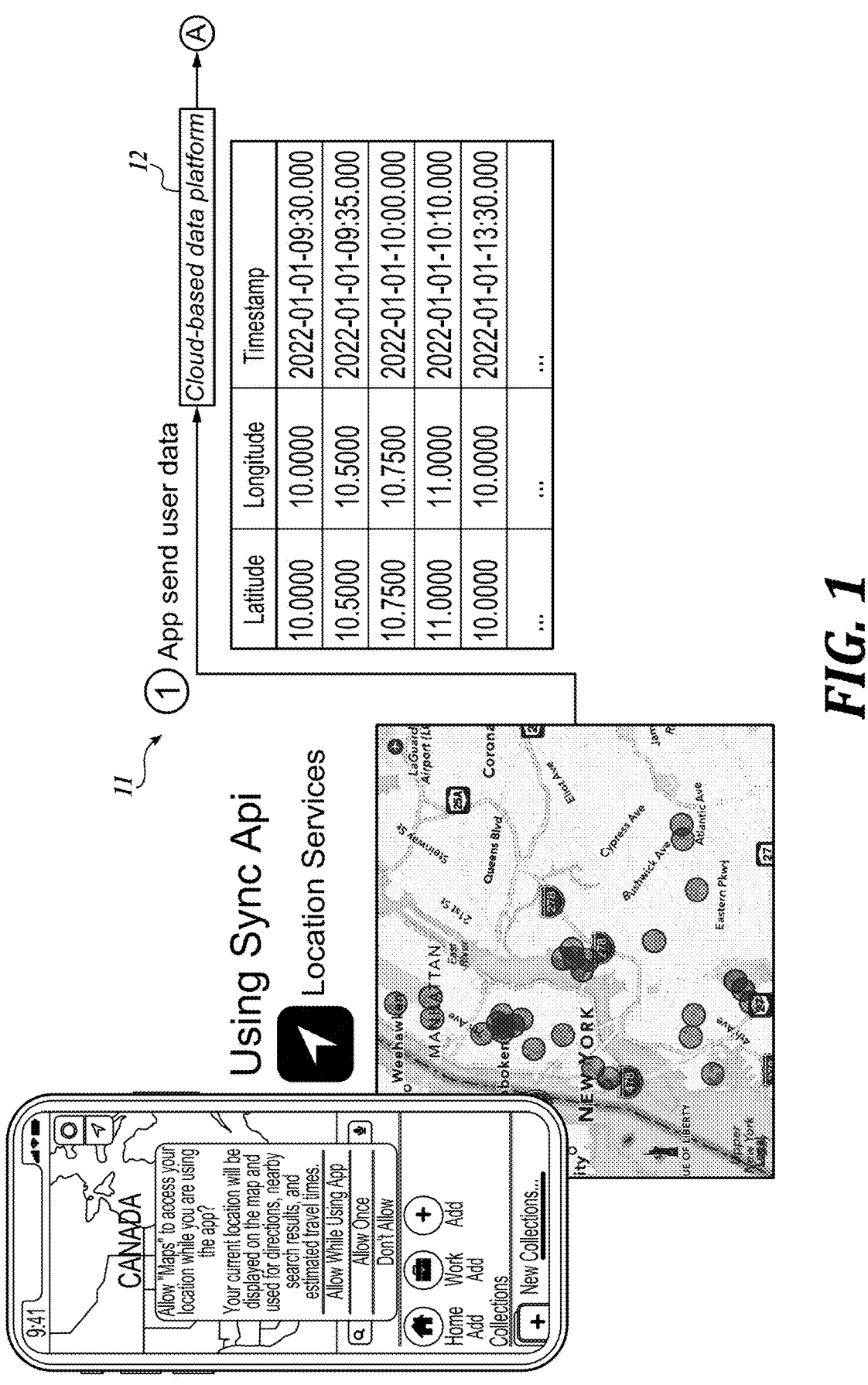
FIG. 1 shows an example for geolocation of a subject via at least a mobile device, estimation of pollution values as determined by an organization that collects and provides environmental exposure information as a service, and communication of a photo-pollution metric ($UVI_{photopollution}$) as a function of UV index (UVI) and the level of a pollutant.
Figure 1:
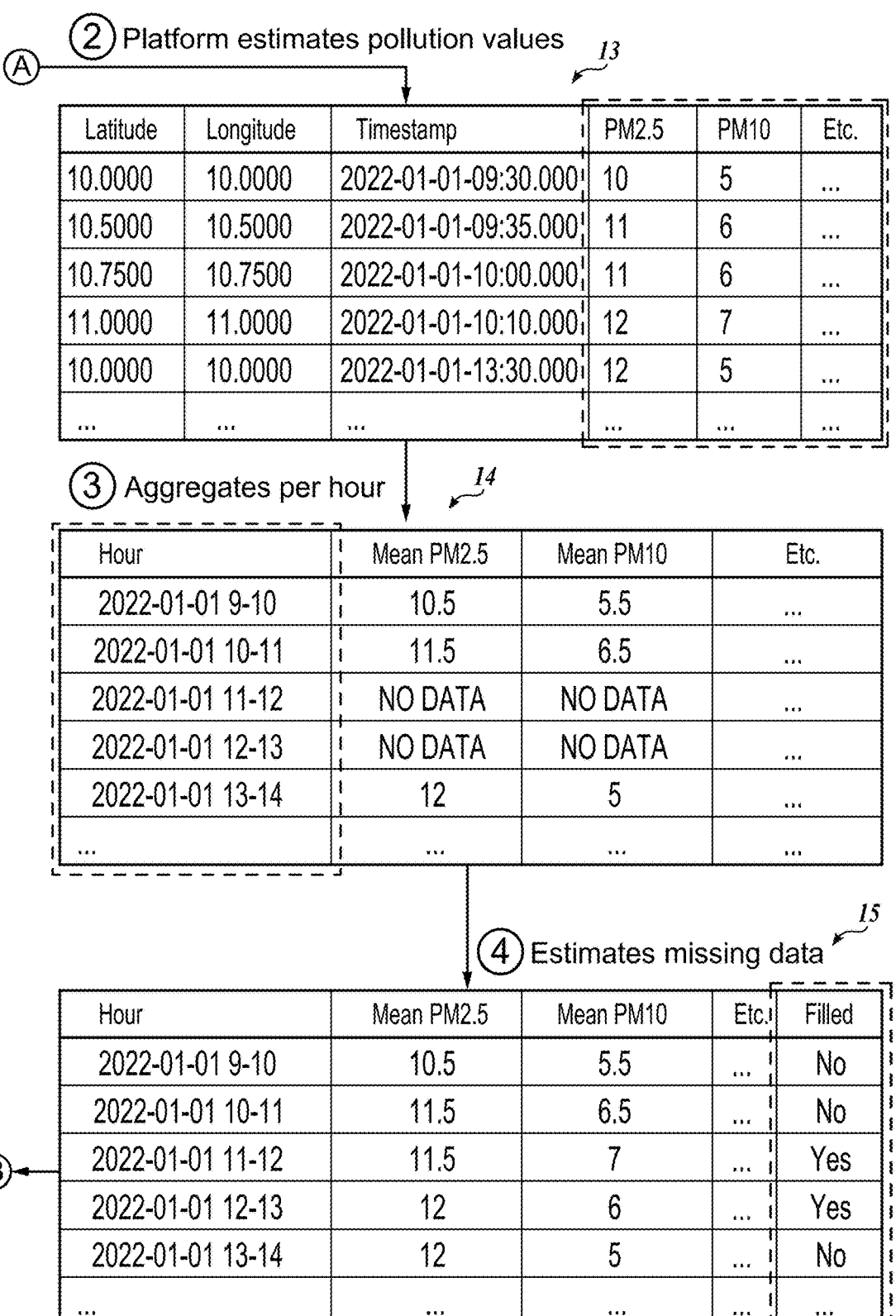

The foregoing aspects and many of the attendant advantages of this invention will become more readily appreciated as the same become better understood by reference to the following detailed description, when taken in conjunction with the accompanying drawings.

DETAILED DESCRIPTION

Scientific literature indicates that the accumulation of pollutant particles (PM2.5, PM10, soot, dust, dirt, etc.), air pollutant gases ($NO_2$, $SO_2$, CO, $O_3$, etc.), solar energy, and pollen particles (tree, grass, weed pollens, etc.) in and on the skin is most directly linked with deleterious skin outcomes. Polycyclic aromatic hydrocarbons (PAH), UVA, UVB, and HEV light also induce skin toxicity. UV index (UVI) is an informative metric for managing exposure to harmful UV radiation and associated risk of skin damage or skin conditions, but this metric fails to account for the influence of environmental pollutants on these risks. As a result, consumers in areas with environmental pollutants that can impact skin health are at a higher risk of receiving skin damage or adverse skin conditions due to the presence of not only UV radiation but also environmental pollutants.

Therefore, there is a need for a geolocation-specific exposome level, and systems and methods for making and using the same, for highly relevant guidance for skin functionality, health, and appearance. A metric should be implemented within the constraints of highly scalable data systems such as environmental variables that are monitored globally at high spatiotemporal resolution, including UVI and pollutant levels. Such a metric should also be easily communicable and understandable to skin health and beauty consumers and require little or no pre-existing knowledge of the effects of environmental exposures on skin. Such a metric could be used as an input into beauty or skincare guidance or recommendations, in any form.

The present disclosure addresses these and other long-felt and unmet needs in the art with a data platform and user experiences implemented with systems, devices, and methods for making and using an environmental metric. The data platform measures the average environmental exposure for each in a series of time intervals, which can range from hourly to monthly temporal resolution. For example, given a smartphone's collected geolocations, corresponding mean values are calculated for each environmental variable. In addition to individual variables, the data platform enables new composite metrics that are relevant for skin health, such as pollution-solar radiation synergy, a novel metric for communicating risk of skin conditions based on environmental exposure. In embodiments, a metric is based on UVI and levels of an environmental pollutant and is tailored to a specific individual with a specific set of geolocation data. In embodiments, the geolocation data is based on global positioning system (GPS) data and/or data obtained from a questionnaire that asks about the individual's historical geolocations.

In an embodiment, the disclosed technologies and methodologies are designed and configured to determine an exposure risk, an exposure severity, an exposure mitigation protocol associated with an exposome-induced skin condition based on a deviation of a determined ultraviolet index (UVI), geolocation-specific pollutant level, and a photo-pollution metric ($UVI_{photopollution}$) from a reference condition. In an embodiment, the system is designed to determine an exposure risk, an exposure severity, an exposure mitigation protocol associated with an exposome-induced skin condition based on a degree of deviation of a determined ultraviolet index (UVI), geolocation-specific pollutant level, and a photo-pollution metric ($UVI_{photopollution}$) from a reference condition.

FIG. 1 depicts an example for determining the geolocation of a subject by at least a mobile device that includes generating an estimation of pollution values as determined by an organization that collects and provides environmental exposure information as a service, and communication of a photo-pollution metric ($UVI_{photopollution}$) as a function of UV index (UVI) and the level of a pollutant.

In embodiments, an application programming interface (API) is used by a software application of an individual's smartphone to access location services of the individual's smartphone, and the software application can process locally or send 11 geolocation data to a cloud-based data platform 12 for further processing. The system estimates 13 pollution values for the geolocations of the geolocation data and may generate aggregates per hour 14 and estimate missing data 15 to ensure a complete environmental data set is utilized. In the shown embodiments, particulate matter is utilized as an environmental pollutant, but other pollutants may be used in an embodiment. PM2.5 levels correspond to levels of particulate matter having a diameter of less than or equal to about 2.5 μm, and PM10 levels correspond to levels of particulate matter having a diameter of less than or equal to about 10 μm.

Once determined, a photo-pollution metric, such as pollution adjusted UVI 17, is optionally presented to the user either alone or in combination with other environmental data 16, in embodiments. In embodiments, the individual may be presented with exposure history which is based on annual exposure levels to pollutants and/or UV radiation, and the information catered or individualized to the user for inclusion of health tips, hourly forecast, air quality warnings, current conditions, and links to articles of information for further reading or consumer education. As shown at FIG. 2, a variety of environmental data 21 are utilized for a metric of a device, system, or method according to the disclosure, however, in embodiments, PM2.5 is utilized in combination with UVI.

Figure 3:
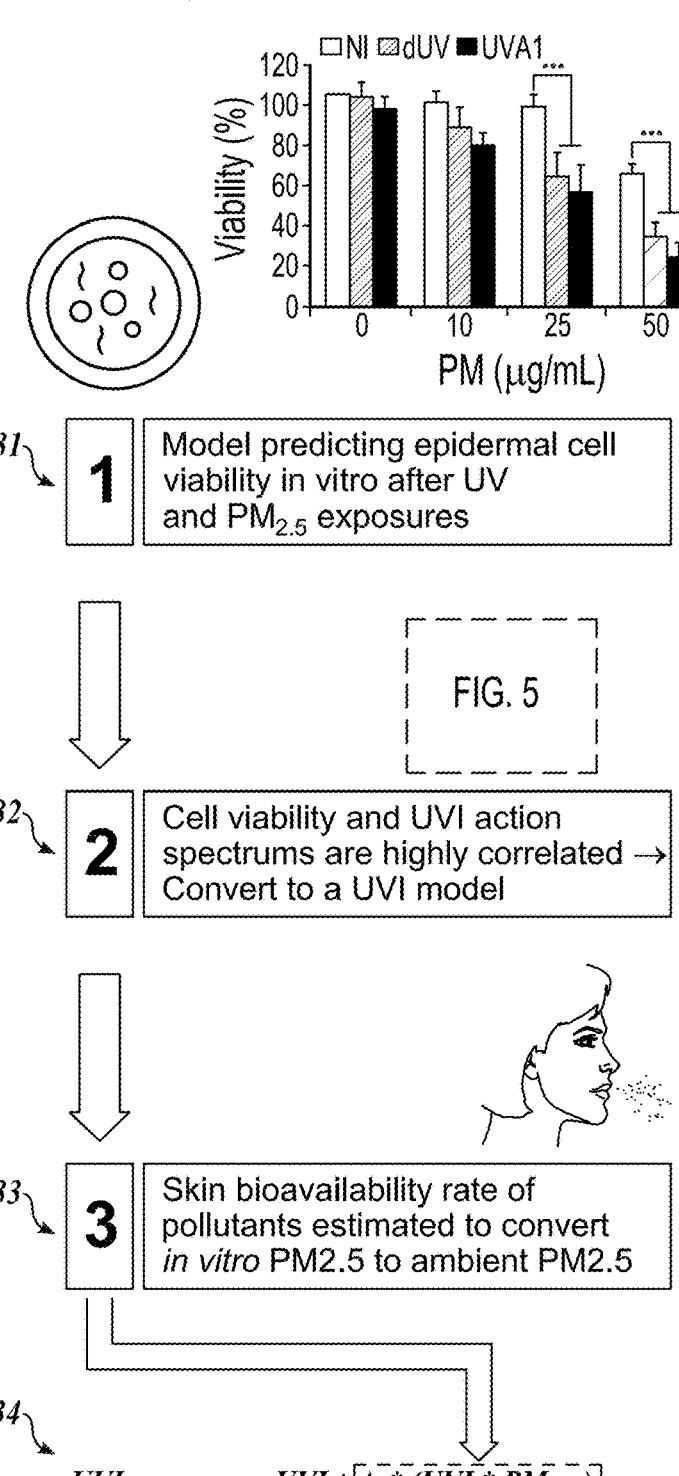
FIG. 3 shows an overview of research methods for formulating the photo-pollution metric ($UVI_{photopollution}$) based on UVI and pollutant levels.

FIG. 3 depicts an overview of a method for formulating the photo-pollution metric ($UVI_{photopollution}$) based on UVI and pollutant levels. A method for formulating a photo-pollution metric for risk of a skin condition using a computational system comprises converting, with the computational system, a cell viability function based on results from exposure of cells to ultraviolet light (UV) and a pollutant in vitro 31 to an ultraviolet index (UVI) linear regression model 32, wherein UVI, pollutant level, and a UVI-pollutant factor are weighted factors in the UVI linear regression model. The UVI-pollutant factor, (UV*PM) or (UV*PM2.5), is weighted based on an estimated bioavailability 33 of the particulate matter. The bioavailability weighted factor, $PM_{bio-dose}$, is determined based on biological characteristics of the subject and the environment, and a determined value for $PM_{bio-dose}$, A, is used for the weight of the UVI-pollutant factor. Once the weights for UVI, PM, and the UVI-pollutant factor (A) are determined, the photo-pollution metric is determined 34.

Figure 4:
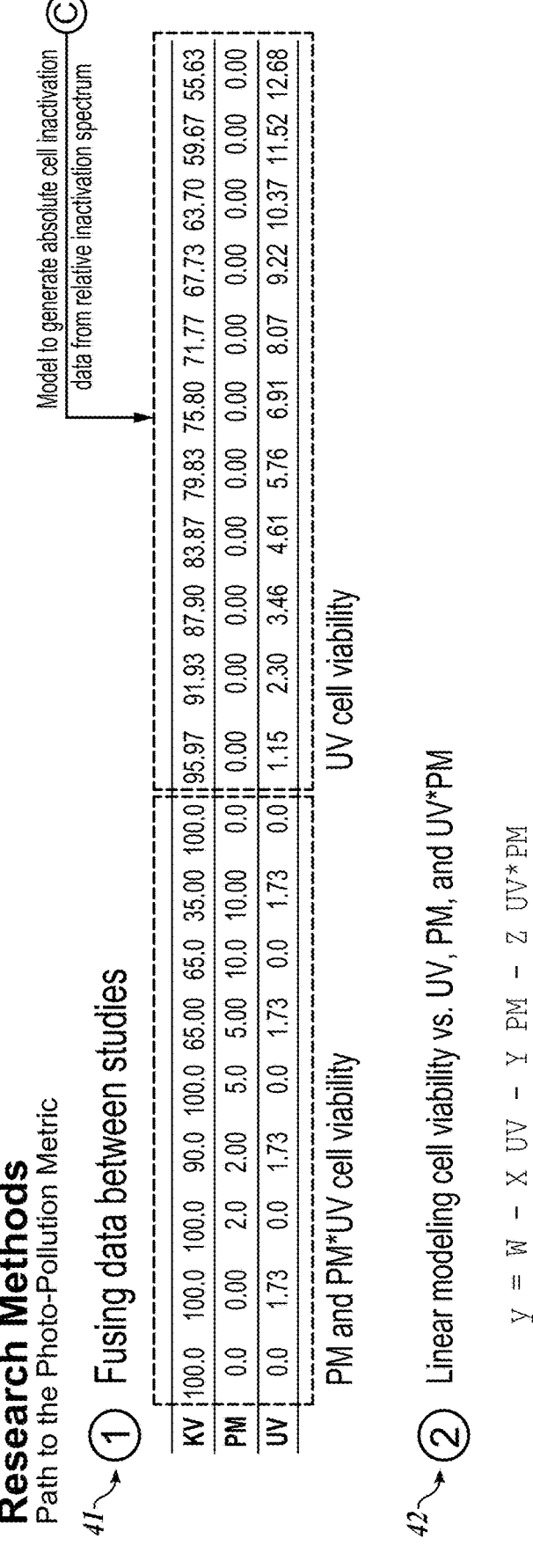
FIG. 4 shows a more detailed view of research methods for formulating the photo-pollution metric.
Figure 4:
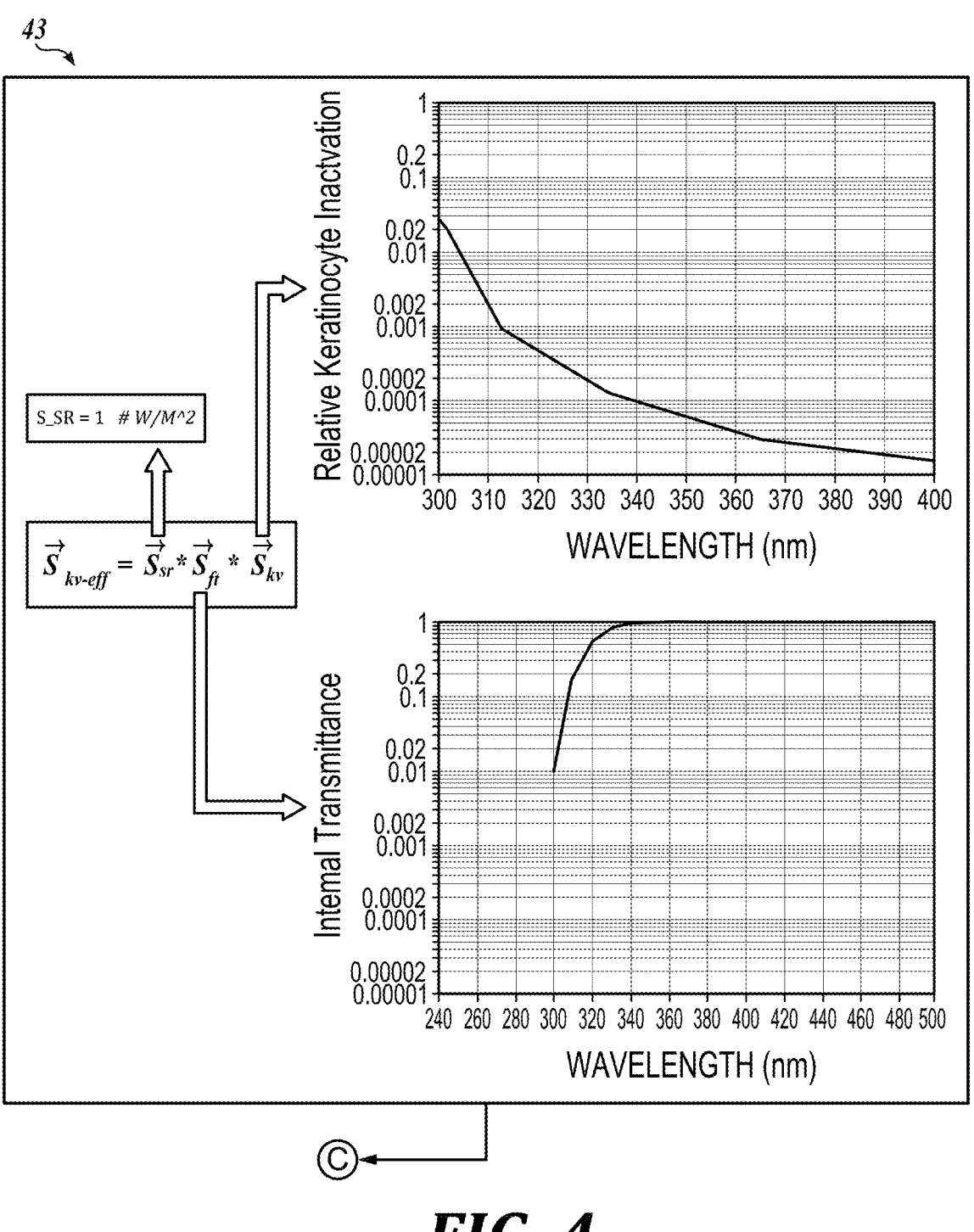

As shown at FIG. 4, a more detailed view of the method for formulating the photo-pollution metric is shown. Briefly, the method includes combining 41 data from one or more experiments exposing cells or tissues to UV radiation (UV), particulate matter (PM), or both (UV*PM), and linearly modeling 42 cell viability versus UV, PM, and UV*PM, and plotting 43 relative keratinocyte inactivation against wavelength of UV light, then translating 44 cell viability model coefficients to a photo-pollution/UVI model. Translating 44 cell viability model coefficients to a photo-pollution/UVI model includes modeling 45 the biological dose of PM in the skin for achieving 46 the photo-pollution metric.

Generally, methods for managing environmental exposure and associated risk of an exposome-induced skin condition of a subject comprise: determining a geolocation-specific exposome level: determining the associated risk of the exposome-induced skin condition based on the geolocation-specific exposome level; and communicating the associated risk of the exposome-induced skin condition to the subject.

FIG. 14 shows an example method 1401 for determining a value of a metric according to the disclosure using a computational system, wherein the function for determining the metric has been established. A personal device provides 1402 personal data comprising geolocations and timestamps to an environmental data service. The environmental data service provides 1403 environmental data comprising UVI and PM2.5 that corresponds with the personal data to the personal device. The personal device determines 1404 a pollution-adjusted UVI metric that corresponds to exposure to UV and pollutants by a person.

Figure 5:
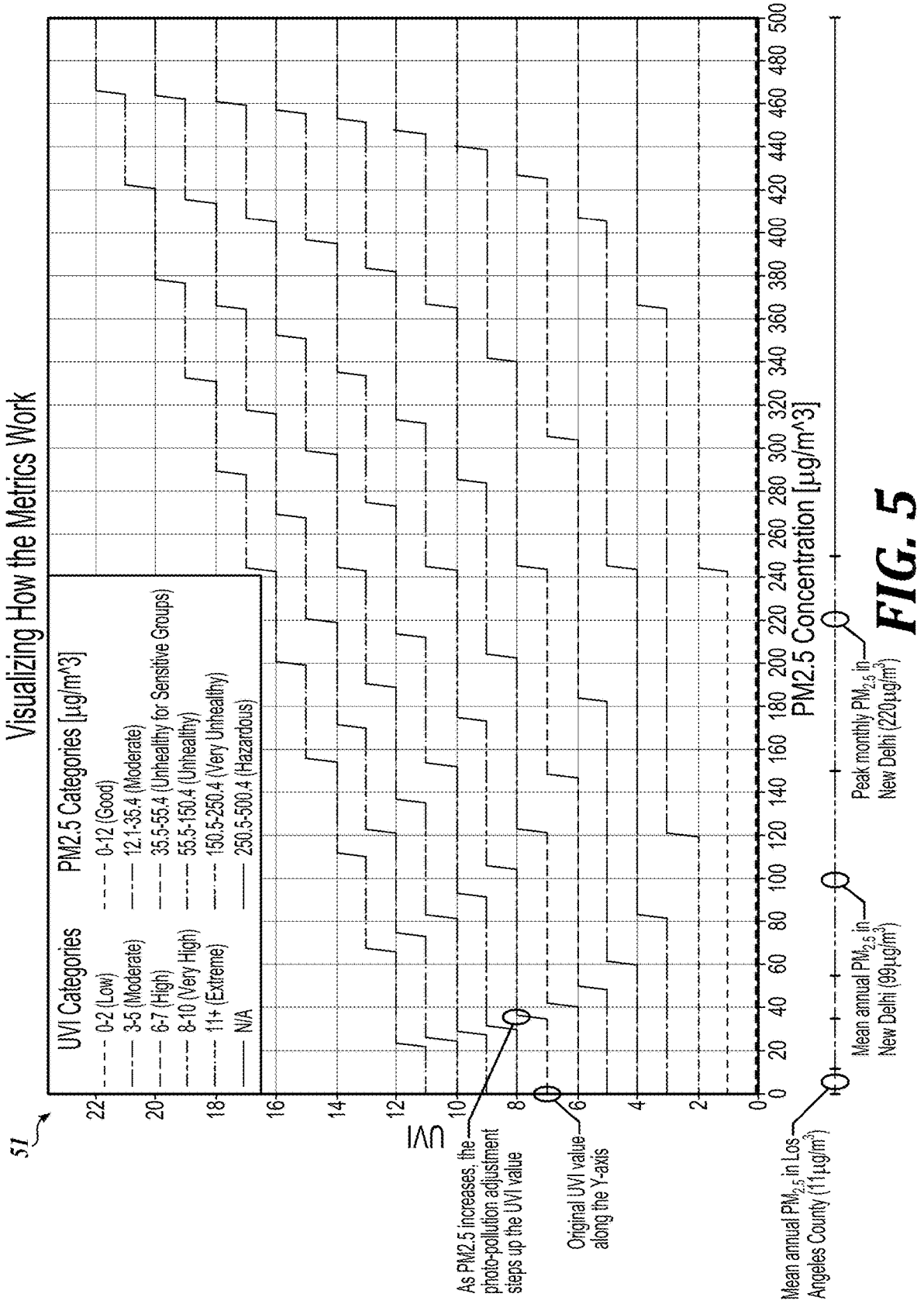
FIG. 5 shows a graph of a photo-pollution metric (y-axis, $UVI_{photopollution}$) as a function of the level of particulate matter having a diameter less than or equal to about 2.5 μm (x-axis, PM2.5 concentration) as influenced by UV index (UVI).

Referring now to FIG. 5, there is shown a graph 51 of a photo-pollution metric (y-axis, $UVI_{photopollution}$) as a function of the level of particulate matter having a diameter less than or equal to about 2.5 μm (x-axis, PM2.5 concentration) as influenced by UV index (UVI). $UVI_{photopollution}$ metric increases with increases in PM2.5, and in particular, $UVI_{photopollution}$ metric increases incrementally with incremental increases in PM2.5.

Figure 7:
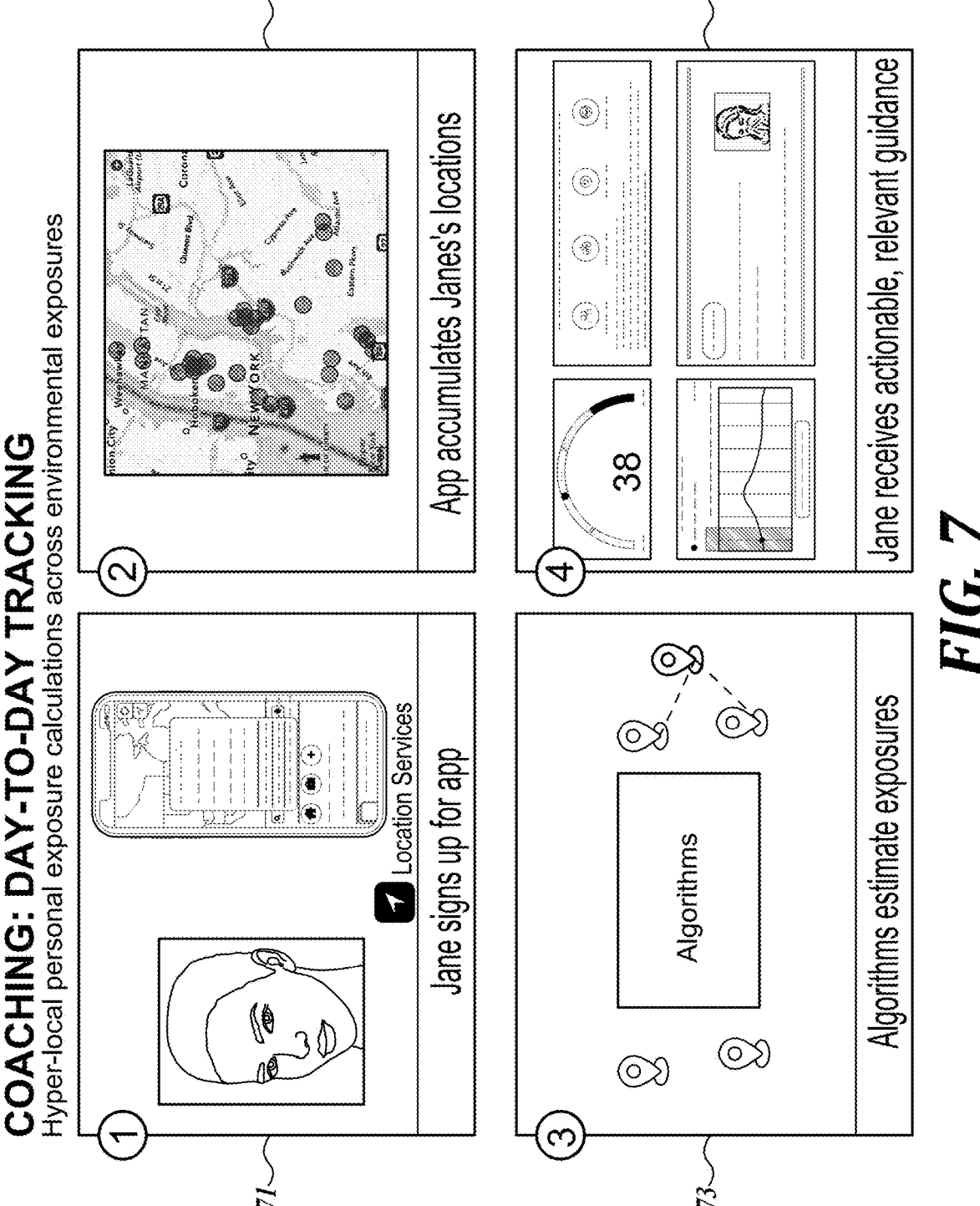
FIG. 7 shows a graphic visualization of an example coaching or day-to-day tracking process that utilizes a software application to track geolocations of a subject and estimate exposure of the subject to environmental pollutants to provide actionable guidance to the subject about healthcare, skincare, and/or outdoor activities.

Referring now to FIGS. 6-8, there are shown graphic visualizations of example uses of the metric in methods, systems, and devices, including an example onboarding process that utilizes a questionnaire to estimate a subject's historical exposures and baseline exposure level (FIG. 6)

and a graphic visualization of an example coaching or day-to-day tracking process that utilizes a software application to track geolocations of a subject and estimate exposure of the subject to environmental pollutants to provide actionable guidance to the subject about healthcare, skincare, and/or outdoor activities (FIG. 7), and several other example uses of the metric for consumer applications (FIG. 8).

An example onboarding process, as shown at FIG. 6, includes steps wherein an individual starts 61 a service for onboarding and the individual completes 62 an initial questionnaire about current and/or prior geolocation information. Questions of the questionnaire can involve current and/or past home and/or work locations, for example. The system then estimates 63 the individual's historical exposures with the metric and the individual can then view 64 their baseline exposure metric and receive actionable guidance or recommendations about how to best use that information, for example, by altering their commute or outside exposure.

An example day-to-day coaching process, as shown at FIG. 7, includes steps wherein the individual signs up 71 for a software application service, the software application accumulates 72 the individual's geolocations, and the software application then estimates exposures 73 utilizing algorithms and methods of the disclosure. The individual can then receive actionable, relevant guidance 74 in the form of the metric, optionally combined with other environmental data.

Figure 9:
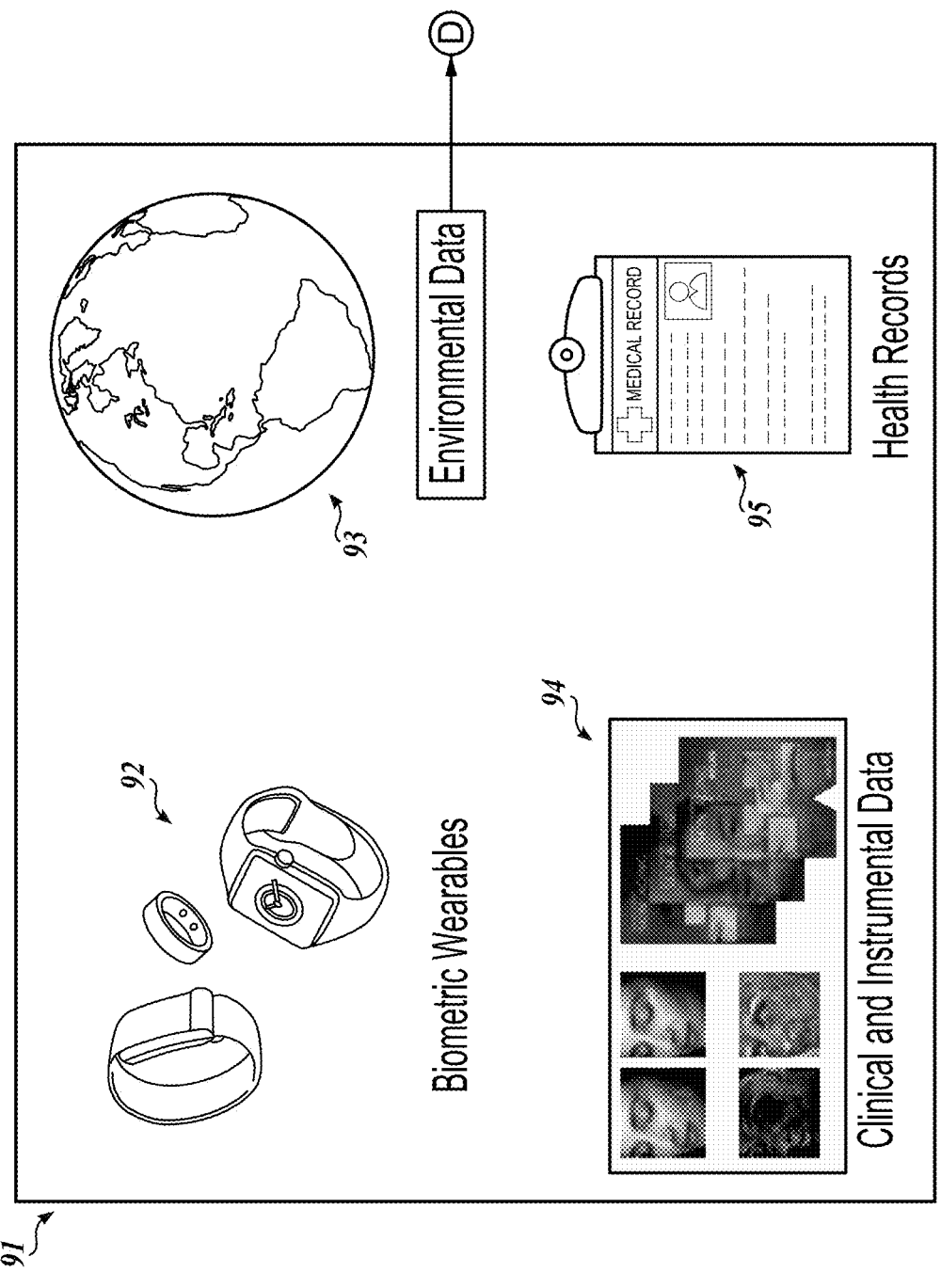
FIG. 9 shows an example application of the metric for clinical studies and healthcare management.

Examples of applications of the environmental exposure metric in research and innovation (R&I) 81 and services 82 are shown at FIG. 8. Example applications include use as an evaluation tool, a data science tool, use in programmatic beauty applications, coaching, and/or diagnostics. As shown at FIG. 9, an example application of the metric for clinical studies and healthcare management 91 can include use of biometric wearable devices 92, use of environmental data 93, use of clinical and instrumental data 94, and use of health records 95. An example set of data 96, that can be captured passively, are used as inputs for clinical studies and healthcare management 91, in embodiments.

Figure 11:
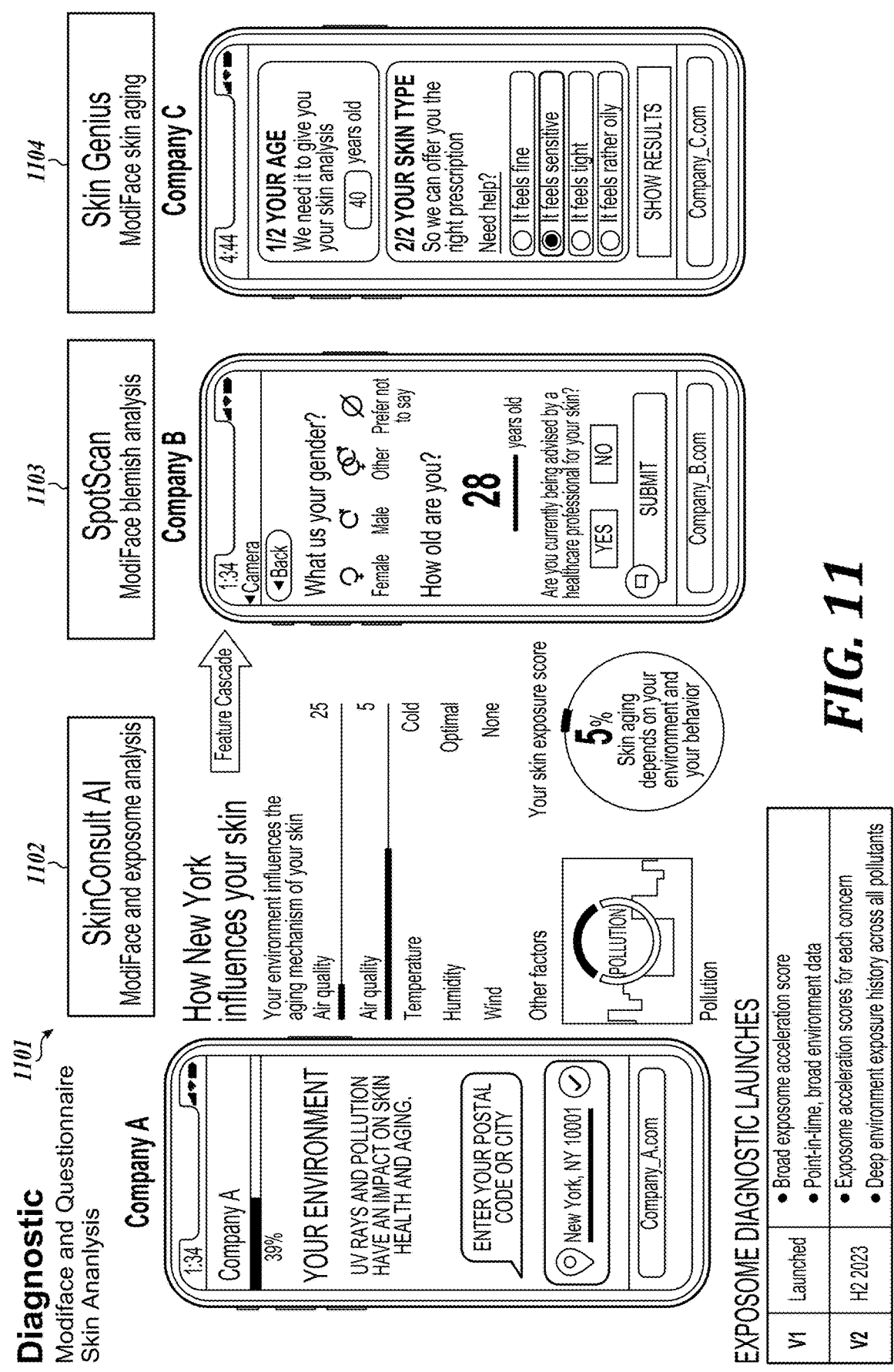
FIG. 11 shows an example diagnostic process that utilizes a questionnaire for a subject to exposome analysis, blemish analysis, and skin aging analysis, with a graphical user interface and/or a feedback interface.
Figure 12:
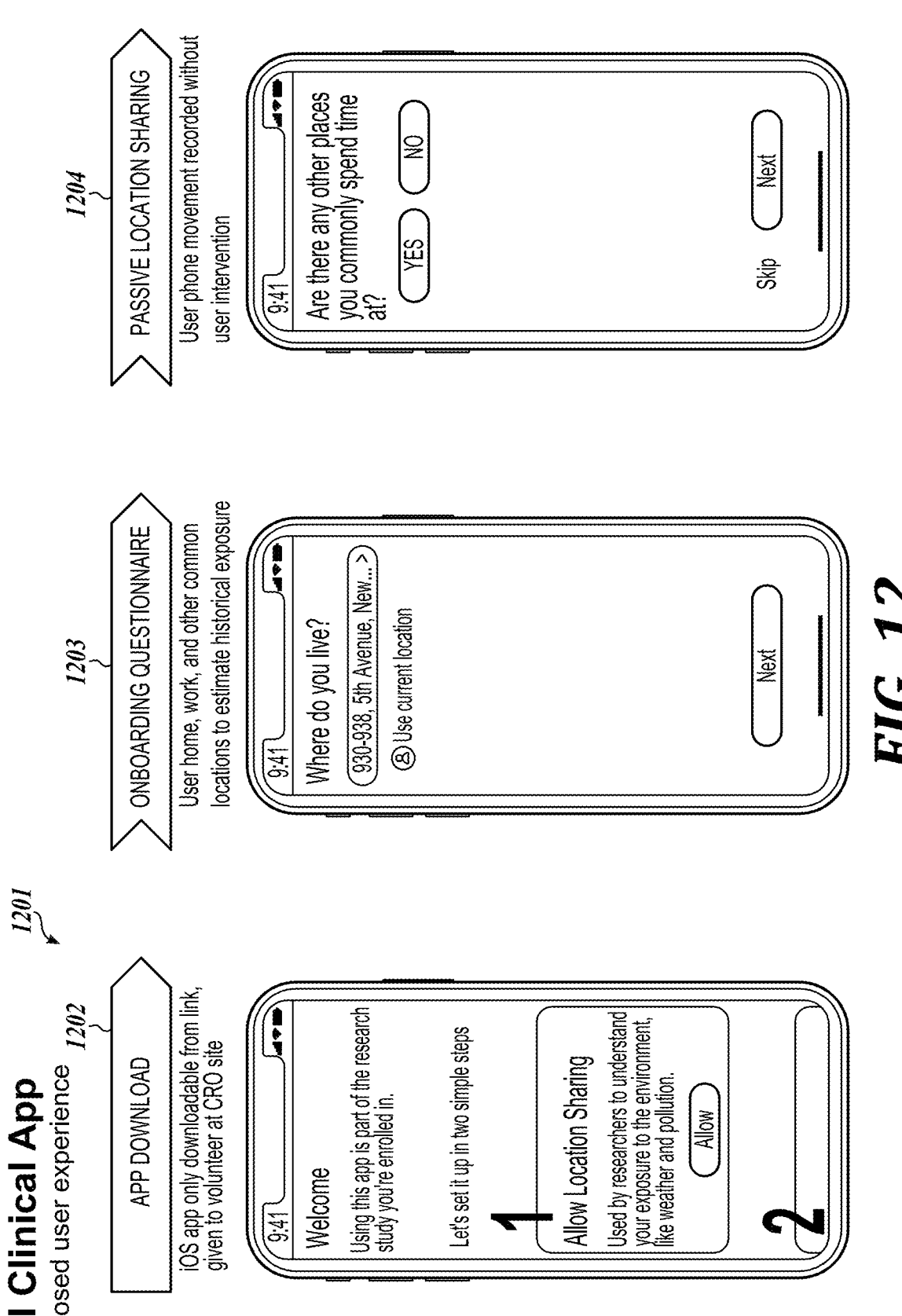
FIG. 12 shows an example clinical study software application user experience wherein a subject participates in an onboarding questionnaire and provides information about past geographical locations and passively shares device geolocation for the clinical study, with a graphical user interface and/or a feedback interface.

Referring now to FIGS. 10-12, there are shown an example application of the metric for exposure to one or more environmental pollutants (e.g., "exposome") for enabling informed decision-making in areas related to their environment, lifestyle, biological processes, and forecasting for potential exposures in the future (FIG. 10), an example diagnostic process that utilizes a questionnaire for a subject to exposome analysis, blemish analysis, and skin aging analysis (FIG. 11), and an example clinical study software application user experience wherein a subject participates in an onboarding questionnaire and provides information about past geographical locations and passively shares device geolocation for the clinical study (FIG. 12).

As shown at FIG. 10, an example software application (e.g., "FaceFacts") can provide an "exposome" focused habit coaching service to beauty consumers. The service can include providing a complete picture of exposures to the individual, providing powerful, personalized, and actionable insights to the individual, and providing a plurality of other features 1001 such as skin forecasts, immediate alerts, exposure reports, and data-driven recommendations for improving healthcare and skincare. In this manner, the individual can make informed decisions regarding health and skincare.

As shown at FIG. 11, an example diagnostic software application and process 1101 is shown. The diagnostic process can request information from the user with one or more app-based web forms wherein the user provides geolocation and receives consultation or advice 1102 from an artificial intelligence (AI), e.g., "SkinConsult AI". The consultation informs the consumer as to how exposure to the environment influences their skin. Features can include a "SpotScan" feature whereby the user's face or skin is scanned by the smartphone to provide analysis (e.g., blemish analysis) and/or a "Skin Genius" feature whereby information about the user's face or skin is provided by the user to a healthcare professional, such as a dermatologist, for evaluation and possible prescription for treatment of a health condition.

As shown at FIG. 12, an example R&I clinical software application is useful for clinical trials or other research that includes tracking individuals' geolocations and environmental exposure information and correlating that information with healthcare conditions and/or treatments, such as experimental or established treatments. The clinical trial or other research can include, among other evaluations, an evaluation of the efficacy of geolocation-based exposure metrics, as described herein, in predicting or correlating with the onset or progression of skin conditions or other health conditions.

Figure 13:
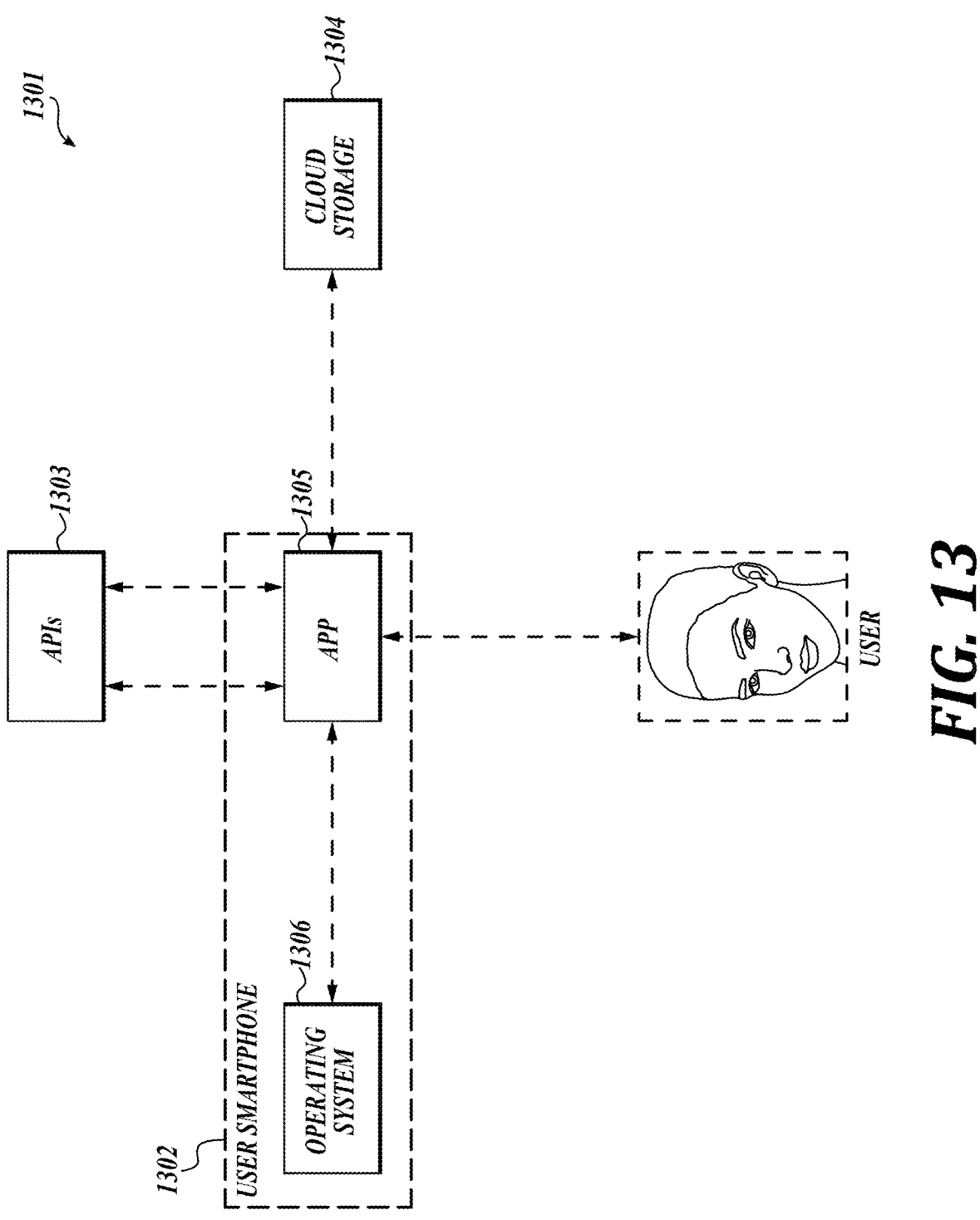
FIG. 13 shows an example computational system in an example configuration for use by a user to view exposure analysis and other information as determined by calculations using the metric.

Referring now to FIG. 13, there is shown an example computational system 1301 in an example configuration for use by a user to view exposure analysis and other information as determined by calculations using the metric: this configuration is used as part of a clinical study, for example. The system 1301 can include a user smartphone 1302 having thereon an operating system 1306 and a software application ("app") 1305. In embodiments, the smartphone is operably connected to a cloud-based data platform accessible via one or more APIs. The smartphone can send geolocation data to the data platform and receive exposure data in return. In embodiments, data collected is stored in the cloud 1304, according to methods known in the art, with one or more networked servers.

Figure 15:
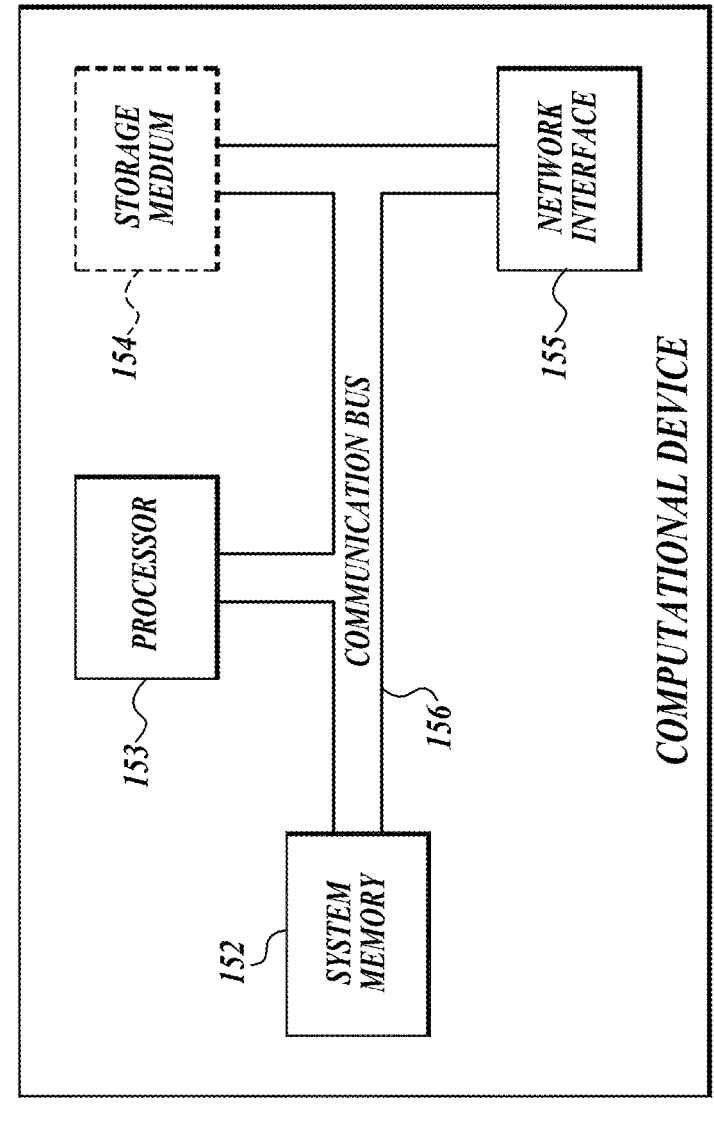
FIG. 15 shows a block diagram that illustrates an example embodiment of a computational device appropriate for use as a computational device or computational system with embodiments of the disclosure.

Referring now to FIG. 15, there is shown a block diagram that illustrates an example embodiment of a computational device 151 appropriate for use as a computational device or computational system with embodiments of the disclosure.

As used herein, "method" refers to a plurality of steps for carrying out an activity or producing a result or effect according to the disclosure. Methods can be fully or partially manual, fully or partially semi-automated, or fully or partially automated, in any degree or combination thereof. Semi-automated and automated methods can be performed in whole or in part by one or more systems of the disclosure.

As used herein, "system" and "computational system" refer to one or more computational devices that are configured for performing all or part of any method of the disclosure, in any order or sequence of steps, optionally in combination with one or more other computational devices that are configured for performing all or part of any method of the disclosure, in any order or sequence of steps. In at least some instances, a method may be performed by two or more computational devices that together form at least part of a computational system, and in such instances, the steps carried out by a first computational device may be complementary to the steps carried out by a second computational device. In other instances, a method may be performed by one computational device that forms at least part of a computational system.

As used herein, "computational device" refers to a physical hardware computing device that is configured for performing all or part of any method of the disclosure, in any order or sequence of steps, optionally with human input.

As shown at FIG. 13, in embodiments, a system 1301 is configured for management of environmental exposure and associated risk of an exposome-induced skin condition of a subject (e.g., user). The system 1301 comprises circuitry (e.g., 1303, 1304) for determining a geolocation-specific exposome level: circuitry (e.g., 1302, 1304, 1305, 1306) for determining the associated risk of the exposome-induced skin condition based on the geolocation-specific exposome level; and circuitry (e.g., 1302, 1305, 1306) for communicating the associated risk of the exposome-induced skin condition to the subject. In embodiments, the circuitry for communicating the associated risk of the exposome-induced skin condition to the subject implements a graphical user interface and/or a feedback interface to communicate with the subject.

In embodiments, the system 1301 comprises circuitry (e.g., 1303, 1304) for determining an ultraviolet index (UVI) and a geolocation-specific pollutant level responsive to one or more inputs indicative of a geolocation of the subject at a time; circuitry (e.g., 1302, 1304, 1305, 1306) for determining a value of a photo-pollution metric ($UVI_{photopollution}$) responsive to one or more inputs indicative of the UVI and the geolocation-specific pollutant level, such that the value of the photo-pollution metric corresponds to an associated exposure risk of the exposome-induced skin condition; and circuitry (e.g., 1302, 1305, 1306) for communicating the associated exposure risk of the exposome-induced skin condition to the subject.

In embodiments, the circuitry for determining the ultraviolet index (UVI) and the geolocation-specific pollutant level (e.g., 1303, 1304) comprises circuitry configured to retrieve the geolocation-specific pollutant level from a remote third-party server (e.g., 1303, 1304) that collects and provides environmental information.

In embodiments, the circuitry for determining the ultraviolet index (UVI) and the geolocation-specific pollutant level (e.g., 1303, 1304) comprises circuitry configured to determine the geolocation via at least a mobile device (e.g., 1302), such that the determining the value of the photo-pollution metric is performed by the mobile device (e.g., 1302) or a server (e.g., 1303, 1304) remote to the mobile device and the communicating the value of the metric is performed by the mobile device (e.g., 1302).

In embodiments, the circuitry for determining the ultraviolet index (UVI) and the geolocation-specific pollutant level (e.g., 1303, 1304) comprises circuitry configured to retrieve geolocation-specific pollutant level information that is associated with particulate matter having a diameter of less than or equal to about 2.5 µm (PM2.5).

In embodiments, the circuitry for determining the ultraviolet index (UVI) and the geolocation-specific pollutant level (e.g., 1303, 1304) comprises circuitry configured to increase $UVI_{photopollution}$ incrementally with incremental increases in PM2.5.

In embodiments, the circuitry for determining the ultraviolet index (UVI) and the geolocation-specific pollutant level (e.g., 1303, 1304) comprises circuitry configured to determine $UVI_{photopollution}$ according to:

$$UVI_{photopollution} = UVI + A*(UVI*PM)$$

wherein: A is a weighted factor that is based on an approximate biological dose of particulate matter in an environment: (UVI*PM) is a UVI-pollutant factor: UVI is UV index; and PM is ambient air concentration of PM2.5 in the environment in $$\frac{\mu g}{m^3}.$$

In embodiments, the circuitry (e.g., 1302, 1305, 1306) for communicating the associated exposure risk of the exposome-induced skin condition to the subject comprises a graphical user interface configured to depict one or more instances of the UVI, the geolocation-specific pollutant level, and/or the $UVI_{photopollution}$ Non-limiting example graphical user interfaces are shown at FIG. 1 (e.g., 16, 17), FIG. 6, FIG. 7, FIG. 10, FIG. 11, and FIG. 12, and are described in more detail elsewhere herein.

In embodiments, the circuitry (e.g., 1302, 1305, 1306) for communicating the associated exposure risk of the exposome-induced skin condition to the subject comprises a graphical user interface configured to depict an exposome history of the subject, an actionable guidance, a health tip, an environmental status, an environmental forecast, and/or an article of information. Non-limiting example graphical user interfaces are shown at FIG. 1, FIG. 6, FIG. 7.

In embodiments, the circuitry (e.g., 1302, 1305, 1306) for communicating the associated exposure risk of the exposome-induced skin condition to the subject comprises the graphical user interface configured to depict the exposome history of the subject and/or the actionable guidance, and the exposome history is determined by presenting a questionnaire to the subject and receiving responses from the subject, via the circuitry for communicating (see, e.g., FIG. 6): or the exposome history is determined by accumulating the subject's historical locations and estimating historical exposure levels based on the subject's historical locations (see, e.g., FIG. 7), via the circuitry for communicating (e.g., 1302, 1305, 1306) or one or both circuitries for determining (e.g., 1302, 1303, 1304, 1305, 1306).

In embodiments, the circuitry for communicating (e.g., 1302, 1305, 1306) the associated exposure risk of the exposome-induced skin condition to the subject comprises a user feedback interface (e.g., an interface of 1302) configured to provide an auditory feedback, a textual feedback, a software app-based feedback, a smartphone vibration feedback, and/or a haptic feedback to the subject, and one or more feedbacks of the user feedback interface are selectable or customizable by the user. The feedback interface may be implemented as a graphical user interface, as described elsewhere herein (e.g., textual, software app-based), and/or may be implemented with other forms of feedback, including but not limited to the aforementioned forms (e.g., auditory, vibration, haptic). In embodiments, the feedback provided by the graphical user interface and/or the feedback interface corresponds to one or more severities of the associated exposure risk of the exposome-induced skin condition. For example, a serious risk of the skin condition due to exposure can be associated with an alert or other feedback that conveys the seriousness of the risk, while a lower risk of the skin condition due to exposure can be associate with an alert or other feedback that conveys the nature of the risk as being relatively lower.

In various aspects, the associated exposure risk of the exposome-induced skin condition is communicated to the subject, via a graphical user interface, as actionable guidance to enable the subject to manage their exposure to one or more pollutants or environmental stressors, or as a recommended action for the subject to manage their exposure to one or more pollutants or environmental stressors. In embodiments, the actionable guidance or recommended action is based on the result of a comparison between two or more geolocation-specific pollutant levels (e.g., a first geolocation-specific pollutant level and a second geolocation-specific pollutant level), such that the user receives information or recommendations for one or more courses of action that would minimize exposure of the user to the one or more pollutants or environmental stressors, if acted upon. For example, an individual receives exposure risk information from the system that corresponds to two different courses of action (e.g., spend time outside at location 'A' or spend time outside at location 'B') and makes informed decisions about time spent outdoors, such as geolocations to avoid to minimize exposure risk, and geolocations that may not need to be avoided that may have a lower exposure risk. In this manner, the system provides relevant and actionable guidance or recommendations to the user and enables better management of exposure risk and better skin health.

While multiple different types of computational devices useful for systems of the disclosure were discussed above or are otherwise envisioned, an example computational device 151 at FIG. 15 describes various elements that are common to many different types of computational devices. While FIG. 15 is described with reference to a computational device that is implemented as a device on a network, the description below is applicable to servers, personal computers, mobile phones, smart phones, tablet computers, embedded computational devices, and other devices that may be used to implement portions of embodiments of the present disclosure. Some embodiments of a computational device may be implemented in or may include an application-specific integrated circuit (ASIC), a field-programmable gate array (FPGA), or other customized device. Moreover, those of ordinary skill in the art and others will recognize that the computational device 151 may be any one of any number of currently available or yet to be developed devices.

In its most basic configuration, the computational device 151 includes at least one processor 153 and a system memory 152 connected by a communication bus 156. Depending on the exact configuration and type of device, the system memory 152 may be volatile or nonvolatile memory, such as read only memory ("ROM"), random access memory ("RAM"), EEPROM, flash memory, or similar memory technology. Those of ordinary skill in the art and others will recognize that system memory 152 typically stores data and/or program modules that are immediately accessible to and/or currently being operated on by the processor 153. In this regard, the processor 153 may serve as a computational center of the computational device 151 by supporting the execution of instructions.

As further illustrated in FIG. 15, the computational device 151 may include a network interface 155 comprising one or more components for communicating with other devices over a network. Embodiments of the present disclosure may access basic services that utilize the network interface 155 to perform communications using common network protocols. The network interface 155 may also include a wireless network interface configured to communicate via one or more wireless communication protocols, such as Wi-Fi, 2G, 3G, LTE, WiMAX, Bluetooth, Bluetooth low energy, and/or the like. As will be appreciated by one of ordinary skill in the art, the network interface 155 illustrated in FIG. 15 may represent one or more wireless interfaces or physical communication interfaces described and illustrated above with respect to particular components of the computational device 151.

In the example embodiment depicted in FIG. 15, the computational device 151 also includes a storage medium 154. However, services may be accessed using a computational device that does not include means for persisting data to a local storage medium. Therefore, the storage medium 154 depicted in FIG. 15 is represented with a dashed line to indicate that the storage medium 154 is optional. In any event, the storage medium 154 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

Suitable implementations of computational devices that include a processor 153, system memory 152, communication bus 156, storage medium 154, and network interface 155 are known and commercially available. For ease of illustration and because it is not important for an understanding of the claimed subject matter, FIG. 15 does not show some of the typical components of many computational devices. In this regard, the computational device 151 may include input devices, such as a keyboard, keypad, mouse, microphone, touch input device, touch screen, tablet, and/or the like. Such input devices may be coupled to the computational device 151 by wired or wireless connections including RF, infrared, serial, parallel, Bluetooth, Bluetooth low energy, USB, or other suitable connections protocols using wireless or physical connections. Similarly, the computational device 151 may also include output devices such as a display, speakers, printer, and the like. Since these devices are well known in the art, they are not illustrated or described further herein.

Non-Limiting Embodiments

While general features of the disclosure are described and shown and particular features of the disclosure are set forth in the claims, the following non-limiting embodiments relate to features, and combinations of features, that are explicitly envisioned as being part of the disclosure. The following non-limiting Embodiments contain elements that are modular and can be combined with each other in any number, order, or combination to form a new non-limiting Embodiment, which can itself be further combined with other non-limiting Embodiments.

Embodiment 1. A method for managing environmental exposure and associated risk of an exposome-induced skin condition of a subject, the method comprising: determining an ultraviolet index (UVI) and a geolocation-specific pollutant level responsive to one or more inputs indicative of a geolocation of the subject at a time; determining a value of a photo-pollution metric ($UVI_{photopollution}$) responsive to one or more inputs indicative of the UVI and the geolocation-specific pollutant level, wherein the value of the photo-pollution metric corresponds to an associated exposure risk of the exposome-induced skin condition; and communicating the associated exposure risk of the exposome-induced skin condition to the subject.

Embodiment 2. The method of any other Embodiment, wherein the determining the ultraviolet index (UVI) and the geolocation-specific pollutant level comprises retrieving the geolocation-specific pollutant level from a remote third-party server that collects and provides environmental information.

Embodiment 3. The method of any other Embodiment, wherein the determining the ultraviolet index (UVI) and the geolocation-specific pollutant level comprises determining the geolocation via at least a mobile device, and wherein the determining the value of the photo-pollution metric is performed by the mobile device or a server remote to the mobile device and the communicating the value of the metric is performed by the mobile device.

Embodiment 4. The method of any other Embodiment, wherein the determining the ultraviolet index (UVI) and the geolocation-specific pollutant level comprises retrieving geolocation-specific pollutant level information that is associated with particulate matter having a diameter of less than or equal to about 2.5 μm (PM2.5).

Embodiment 5. The method of any other Embodiment, wherein the determining the ultraviolet index (UVI) and the geolocation-specific pollutant level results in $UVI_{photopollution}$ that increases incrementally with incremental increases in PM2.5.

Embodiment 6. The method of any other Embodiment, wherein the determining the ultraviolet index (UVI) and the geolocation-specific pollutant level comprises determining $UVI_{photopollution}$ according to:

$$UVI_{photopollution} = UVI + A*(UVI*PM)$$

wherein: A is a weighted factor that is based on an approximate biological dose of particulate matter in an environment: (UVI*PM) is a UVI-pollutant factor: UVI is UV index; and PM is ambient air concentration of PM2.5 in the environment in $$\frac{\mu g}{m^3}.$$

Embodiment 7. The method of any other Embodiment, wherein the communicating the associated exposure risk of the exposome-induced skin condition to the subject occurs via a graphical user interface configured to depict one or more instances of the UVI, the geolocation-specific pollutant level, and/or the $UVI_{photopollution}$.

Embodiment 8. The method of any other Embodiment, wherein the communicating the associated exposure risk of the exposome-induced skin condition to the subject comprises generating one or more instances indicative of an exposome history of the subject, an exposure risk of the exposome-induced skin condition to the subject, a severity measure of the exposure risk of the exposome-induced skin condition to the subject, a user-selectable menu including one or more actionable risk mitigation actions, a health tip, an environmental status, an environmental forecast, and/or an article of information on a graphical user interface.

Embodiment 9. The method of any other Embodiment, wherein the communicating the associated exposure risk of the exposome-induced skin condition to the subject occurs via the graphical user interface configured to depict the exposome history of the subject and/or the actionable guidance, and wherein the exposome history is determined by presenting a questionnaire to the subject and receiving responses from the subject: or wherein the exposome history is determined by accumulating the subject's historical locations and estimating historical exposure levels based on the subject's historical locations.

Embodiment 10. The method of any other Embodiment, wherein the communicating the associated exposure risk of the exposome-induced skin condition to the subject occurs via a user feedback interface configured to provide an auditory feedback, a textual feedback, a software app-based feedback, a smartphone vibration feedback, and/or a haptic feedback to the subject: wherein one or more feedbacks of the user feedback interface are selectable or customizable by the user.

Embodiment 11. The method of any other Embodiment, wherein the communicating the associated exposure risk of the exposome-induced skin condition to the subject occurs via a user feedback interface configured to provide one or more feedbacks that correspond to one or more severities of the associated exposure risk of the exposome-induced skin condition.

Embodiment 12. The method of any other Embodiment, wherein a first geolocation-specific pollutant level corresponds with a first feedback and a first severity of the associated exposure risk of the exposome-induced skin condition; and wherein a second geolocation-specific pollutant level corresponds with a second feedback and a second severity of the associated exposure risk of the exposome-induced skin condition; wherein the first geolocation-specific pollutant level is different from the second geolocation-specific pollutant level and the first feedback differs from the second feedback to communicate a difference in the associated exposure risk of the exposome-induced skin condition to the subject.

Embodiment 13. The method of any other Embodiment, wherein the associated exposure risk of the exposome-induced skin condition is communicated to the subject, via a graphical user interface, as actionable guidance to enable the subject to manage their exposure to one or more pollutants or environmental stressors or as a recommended action for the subject to manage their exposure to one or more pollutants or environmental stressors.

Embodiment 14. A method for managing environmental exposure and associated risk of an exposome-induced skin condition of a subject, the method comprising: determining a geolocation-specific exposome level: determining the associated risk of the exposome-induced skin condition based on the geolocation-specific exposome level; and communicating the associated risk of the exposome-induced skin condition to the subject.

Embodiment 15. The method of any other Embodiment, wherein the communicating the associated exposure risk of the exposome-induced skin condition to the subject occurs via a graphical user interface configured to depict an exposome history of the subject, an actionable guidance, a health tip, an environmental status, an environmental forecast, and/or an article of information.

Embodiment 16. The method of any other Embodiment, wherein the communicating the associated exposure risk of the exposome-induced skin condition to the subject occurs via the graphical user interface configured to depict the exposome history of the subject and/or the actionable guidance, and wherein the exposome history is determined by presenting a questionnaire to the subject and receiving responses from the subject: or wherein the exposome history is determined by accumulating the subject's historical locations and estimating historical exposure levels based on the subject's historical locations.

Embodiment 17. The method of any other Embodiment, wherein the communicating the associated exposure risk of the exposome-induced skin condition to the subject occurs via a user feedback interface configured to provide an auditory feedback, a textual feedback, a software app-based feedback, a smartphone vibration feedback, and/or a haptic feedback to the subject; wherein one or more feedbacks of the user feedback interface are selectable or customizable by the user.

Embodiment 18. The method of any other Embodiment, wherein the communicating the associated exposure risk of the exposome-induced skin condition to the subject occurs via a user feedback interface configured to provide one or more feedbacks that correspond to one or more severities of the associated exposure risk of the exposome-induced skin condition.

Embodiment 19. The method of any other Embodiment, wherein a first geolocation-specific pollutant level corresponds with a first feedback and a first severity of the associated exposure risk of the exposome-induced skin condition; and wherein a second geolocation-specific pollutant level corresponds with a second feedback and a second severity of the associated exposure risk of the exposome-induced skin condition; wherein the first geolocation-specific pollutant level is different from the second geolocation-specific pollutant level and the first feedback differs from the second feedback to communicate a difference in the associated exposure risk of the exposome-induced skin condition to the subject.

Embodiment 20. The method of any other Embodiment, wherein the associated exposure risk of the exposome-induced skin condition is communicated to the subject, via a graphical user interface, as actionable guidance to enable the subject to manage their exposure to one or more pollutants or environmental stressors or as a recommended action for the subject to manage their exposure to one or more pollutants or environmental stressors.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for managing environmental exposure and associated risk of an exposome-induced skin condition of a subject, the method comprising:

receiving, by a mobile computing device, global positioning system (GPS) data indicative of a geolocation of the subject and an ultraviolet index (UVI);

determining, by the mobile computing device, a geolocation-specific exposome level based on the GPS data received by the mobile computing device, the geolocation-specific exposome level comprising a geolocation-specific pollutant level;

determining, by the mobile computing device, the associated risk of the exposome-induced skin condition based on the geolocation-specific exposome level by determining a value of a photo-pollution metric ($UVI_{photopollution}$) based on the UVI and the geolocation-specific pollutant level; and communicating, by the mobile computing device, the associated risk of the exposome-induced skin condition to the subject via a graphical user interface.

2. The method of claim 1, wherein the communicating the associated exposure risk of the exposome-induced skin condition to the subject comprises depicting an exposome history of the subject, an actionable guidance, a health tip, an environmental status, an environmental forecast, and/or an article of information.

3. The method of claim 2, wherein the exposome history is determined by presenting a questionnaire to the subject and receiving responses from the subject; or wherein the exposome history is determined by accumulating the subject's historical locations and estimating historical exposure levels based on the subject's historical locations.

4. The method of claim 1, wherein the communicating the associated exposure risk of the exposome-induced skin condition to the subject further comprises providing an auditory feedback, a textual feedback, a software app-based feedback, a smartphone vibration feedback, and/or a haptic feedback to the subject.

5. The method of claim 1, wherein the communicating the associated exposure risk of the exposome-induced skin condition to the subject comprises providing one or more feedbacks that correspond to one or more severities of the associated exposure risk of the exposome-induced skin condition.

6. The method of claim 5, wherein a first geolocation-specific pollutant level corresponds with a first feedback and a first severity of the associated exposure risk of the exposome-induced skin condition; and wherein a second geolocation-specific pollutant level corresponds with a second feedback and a second severity of the associated exposure risk of the exposome-induced skin condition;

wherein the first geolocation-specific pollutant level is different from the second geolocation-specific pollutant level and the first feedback differs from the second feedback to communicate a difference in the associated exposure risk of the exposome-induced skin condition to the subject.

7. The method of claim 1, wherein the associated risk of the exposome-induced skin condition is communicated to the subject, via the graphical user interface, as actionable guidance to enable the subject to manage their exposure to one or more pollutants or environmental stressors or as a recommended action for the subject to manage their exposure to one or more pollutants or environmental stressor.

8. The method of claim 1 further comprising retrieving geolocation-specific pollutant level information that is associated with particulate matter having a diameter of less than or equal to about 2.5 μm (PM2.5).

9. The method of claim 8, wherein the determining the geolocation-specific pollutant level results in $UVI_{photopollution}$ that increases incrementally with incremental increases in PM2.5.

10. The method of claim 8, wherein determining the value of $UVI_{photopollution}$ is obtained according to:

$$UVI_{photopollution} = UVI + A*(UVI*PM)$$

wherein:

A is weighted factor that is based on an approximate biological dose of particulate mater in an environment;

(UVI*PM) is a UVI-pollutant factor; and

PM is ambient air concentration of PM2.5 in the environment in $$\frac{\mu g}{m^3}.$$

* * * * *